United States Patent
Ciapetti et al.

(10) Patent No.: US 7,354,918 B2
(45) Date of Patent: Apr. 8, 2008

(54) DERIVATIVES OF 14.15-DIHYDRO 20.21-DINOREBURNAMENIN-14-OL AND APPLICATIONS THEREOF

(75) Inventors: Paola Ciapetti, Altorf (FR); Laurence Deyon, Illkirch (FR); Camille-Georges Wermuth, Strasbourg (FR); Jean-François Pujol, Paris (FR); Dinah Weissmann, Paris (FR)

(73) Assignee: Biocortech, Paris (FR)

( * ) Notice: Subject to any disclaimer, the term of this patent is extended or adjusted under 35 U.S.C. 154(b) by 0 days.

(21) Appl. No.: 11/581,950

(22) Filed: Oct. 13, 2006

(65) Prior Publication Data

US 2007/0088046 A1 Apr. 19, 2007

Related U.S. Application Data

(63) Continuation of application No. PCT/FR2005/000902, filed on Apr. 14, 2005.

(30) Foreign Application Priority Data

Apr. 14, 2004 (FR) .................................. 04 03873

(51) Int. Cl.
A61K 31/5377 (2006.01)
A61K 31/4375 (2006.01)
C07D 413/14 (2006.01)
C07D 471/22 (2006.01)

(52) U.S. Cl. .................. 514/233.2; 544/125; 544/361; 546/51; 514/253; 514/283

(58) Field of Classification Search ............. 514/233.2, 514/253, 283; 544/125, 361; 546/51
See application file for complete search history.

(56) References Cited

U.S. PATENT DOCUMENTS

| 3,755,335 | A | 8/1973 | Thai et al. |
| 3,937,709 | A | 2/1976 | Sevenet et al. |
| 4,011,330 | A | 3/1977 | Guidicelli et al. |
| 4,057,550 | A | 11/1977 | Szantay et al. |
| 4,291,038 | A | 9/1981 | Farcilli et al. |
| 5,034,396 | A * | 7/1991 | Aktogu et al. ............... 514/283 |

FOREIGN PATENT DOCUMENTS

| EP | 0 317 426 | 5/1989 |
| EP | 0 317 427 | 5/1989 |
| FR | 2 190 113 | 1/1974 |
| FR | 2 285 882 | 4/1976 |
| FR | 2 312 245 | 12/1976 |
| FR | 2 433 528 | 2/1977 |
| FR | 2 381 048 | 9/1978 |
| WO | WO 89/04830 | 6/1989 |

OTHER PUBLICATIONS

Ginovart N, Marcel D, Bezin L, Garcia C, Gagne C, Pujol JF, Weissmann D., "Tyrosine hydroxylase expression within Balb/c and C57black/6 mouse locus coeruleus. I. Topological organisation and phenotypic plasticity of the enzyme-containing cell population", Brain Res. May 20, 1996; 721 (1-2): 11-21.

Ginovart N, Marcel D, Bezin L, Gagne C, Pujol JF, Weissmann D., "Tyrosine hydrolaxylase expression within Balb/c and C57black/6 mouse locus coeruleus. II. Quantitative study of the enzyme level", Brain Res. May 6, 1996; 719(1-2): 45-55.

Weissmann D, Labatut R, Richard F, Rousset C, Pujol JF, "Direct transfer into nitrocellulose and quantitative radioautographic anatomical determination of brain tyrosine hydroxylase protein concentration", J. Neurochem. Sep. 1989; 53 (3): 793-9.

Bourde O., Schmitt P and Pujol JF, "Long-term effect of RU24722 on tyrosine hydroxylase protein concentration on the locus coeruleus of mice: Differential results in Balb/c, C57BL/6 and their CB6 F1 hybrid", Neurochem Int. 1991, 19, (1), 25-31.

Labatut R, Richard F, Milne B, Quntin L, Lecestre D, Pujol JF. "Long-term effects of RU24722 on tyrosine hydroxylase of the rat brain", J. Neurochem. Nov. 1988; 51(5):1367-74.

Schmitt P, Reny-Palasse V, Bourde O, Garcia C, Pujol JF, "Further characterisation of the long-term effect of RU24722 on tyrosine hydroxylase in the rat locus coeruleus", J. Neurochem. Oct. 1993; 61(4): 1423-9.

(Continued)

Primary Examiner—Charanjit S. Aulakh
(74) Attorney, Agent, or Firm—Dorsey & Whitney LLP; Scott D. Rothenberger

(57) ABSTRACT

The invention relates to novel derivatives of 14,15-dihydro 20,21-dinoreburnamenin-14-ol, having formula (I)

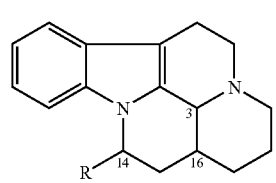

in which R represents a radical —AR' wherein A represents a heteroatom and R' represents a group selected from the group comprising linear or branched $C_1$-$C_6$ alkyl radicals, $C_2$-$C_6$ alkenyls, $C_2$-$C_6$ alkynyls, arylalkyls; esters comprising the formula —$R_1$— CO—O—$R_2$; amides comprising the formula —$R_3$—CO—NZY, wherein Y and Z together can form a cycloalkyl radical or a heterocyclic radical, optionally substituted by one or more alkyl radicals; a radical selected from the group comprising alkyl radicals, alkenyls or alkynyls, substituted by at least one amine with formula —NZY; or one of the pharmaceutically-acceptable salts thereof, including the isomers, enantiomers and diastereoisomers thereof and mixtures thereof. The invention also relates to the use of the novel derivatives for the preparation of a pharmaceutical composition which is intended, in particular, for the treatment and/or prevention of depression, sleep-wake cycle disorders and symptomatic frontal disorders in cognitive components among humans.

20 Claims, 3 Drawing Sheets

OTHER PUBLICATIONS

X. Liu and H.K. Gershenfeld, "Genetic Differences in the Tail-Suspension Test and Its Relationship to Imipramine Response among 11 Inbred Strains of Mice", Biol. Psychiatry 2001 49, 575-581.

J.S. Allard Y Tizabio, JP Shaffery, C.O. Trouth, K. Manabe, "Stereological analysis of hypothalamic hypocretin/orexin neurons in animal models of depression", Neuropeptides 2004, 38, 311-315.

D. Chabas, S. Taheri, C. Renier, and E. Mignot, "The genetic narcolepsie", An Rev. Genomics Human Genet. 2003, 4, 459-83.

Arango V, Underwood MD, Mann J., "Fewer pigmented locus coeruleus neurons in suicide victims: preliminary results", Biol Psychiatry 1996, 39 112-120.

Mann J.J., "Neurobiology of suicidal behavior", Nature Reviews/Neuroscience 4, 2003, 820-28.

Marc R. Mariena, Francis C. Colpaerta, Alan C. Rosenquist, "Noradrenergic mechanisms in neurodegenerative diseases: a theory", Brain Research Reviews 45 (2004) 38-78.

M. Gesi, P. Soldani, F-S Giorgi, A. Santinami, I. Bonaccorsi and F. Fornai, "The role of the locus coeruleus in the development of Parkinson's disease", Neuroscience & Biobehavioral Reviews, vol. 24, Issue 6, Aug. 2000, pp. 655-668.

Kettera T A and Drevets WC, Clinical Neuroscience Research 2 (2002) 182-192, "Neuroimaging studies of bipolar depression: functional neuropathology, treatment effects, and predictors of clinical response" Clinical Neuroscience Research 2 (2002) 182-192.

Ronald C. Petersen, "Mild cognitive impairment: clinical trials", Nature reviews, Drug Discovery vol. 2, Aug. 2003 647.

Vjera A. Holthoff, Bettina Beuthien-Baumann, Elke Kalbe, Susanne Lüdecke, Olaf Lenz, Gerhard Zündorf, Sebastian Spirling, Kristin Schierz, Peter Winiecki, Sandro Sorbi and Karl Herholz, "Regional Cerebral Metabolismin Early Alzheimer's Disease with Clinically Significant Apathy or Depression", Biol Psyschiatry 2005;57: 412-421.

Eve M. Valera, Stephen V. Faraone, Joseph Biederman, Russel A. Poldrack, and Larry J. Seidman, "Functional Neuroanatomy of Working Memory in Adults with Attention-Deficit/Hyperactivity Disorder", Biol Psychiatry 2005;57: 439-447.

J.D. Cohen R. Ganguli C. Carter J. Brar T Nichols M. DeLeo M. Mintun, "Hypofrontality and working memory dysfunction in schizophrenia", Biological Psychiatry, vol. 37, Issue 9, May 1, 1995, p. 633.

The fourth edition of the Diagnostic and Statistical Manual of mental Disorder-American Psychiatric Association Publisher. Washington DC.

Fava M, Davidson KG., "Definition and epidemiology of treatment-resistant depression", Psychiatry Clin North Am. Jun. 1996; 19(2): 179-200.

Lancet, "Efficacy and Safety of Electroconvulsive Therapy in Depression Disorders: A Systematic Review and meta-Analysis", The UK ECT Review Group, Mar. 8, 2003, The Lancet, vol. 361, pp. 799-808.

Couturier J.L., "Efficacy of Rapid-Rate Repetitive Transcranial Magnetic Stimulation in the Treatment of Depression: A Systematic Review and Meta-Analysis", J. Psychiatry Neurosci., Mar. 2005, 30(2), pp. 83-90.

Sackeim, H.A. et al., "Vagus Nerve Stimulation (VNS™) for Treatment-Resistant Depression: Efficacy, Side Effects, and Predictors of Outcome", Neuropsychopharmacology 2001, vol. 25, No. 5; pp. 25, 713-728.

Mayberg, H.S., et al., "Deep Brain Stimulation for Treatment-Resistant Depression", Neuron, vol. 45, pp. 651-660, Mar. 2005.

* cited by examiner

DERIVATIVES OF 14.15-DIHYDRO 20.21-DINOREBURNAMENIN-14-OL AND APPLICATIONS THEREOF

CROSS REFERENCE TO RELATED APPLICATION(S)

This application is a continuation of International application number PCT/FR2005/000902, filed Apr. 14, 2005, which claims priority to French Patent Application FR 0403873, filed Apr. 14, 2004, the contents of both are incorporated herein by reference in their entirety.

FIELD OF THE INVENTION

The purpose of the invention is new derivatives of 14,15-dihydro 20,21-dinoreburnamenin14-ol, and their applications as a drug for Human.

BACKGROUND OF THE INVENTION

Depression is one of the most frequent psychological problems. In France, the proportion of depressive people is 14.9%, including one third of whom are not treated medically. One woman out of five is affected. The prevalence of declared depression has increased by a factor of 6 since 1970. The proportion of depressive persons increased between 1992 and 1997, particularly among the young from 20 to 29 years old (+65%). Therefore, it is particularly important to find treatments better adapted to depression, particularly since some patients may not respond to classical antidepressants.

Derivatives of 20,21-dinoreburnamenin, including 14,15-dihydro 20,21-dinoreburnamenin14-ol, are already known for their vaso-expanding properties, particularly cerebral, and for their activity in regulation of tyrosine hydroxylase in the locus coeruleus (Bourde et al., Neurochem. Int., 23 (6), 567-574, 1993). They are used for cerebral vasculopathies and for all syndromes caused by alteration of cerebral circulation. These derivatives and their first known therapeutic application were described in patent application FR 2 381 048, published on Sep. 15, 1978. This patent application was described in the additive certificate application FR 2 433 528 published on Mar. 14, 1980.

More particularly, application FR 2 381 048 describes derivatives of 20,21-dinoreburnamenin and their preparation process. The pharmacological properties of these compounds are also described: these compounds are valuable cerebral oxygenators and vasoregulators that in particular increase cerebral flow in the cerebral microcirculation. Application FR 2 433 528 also describes the process for preparation of a particular isomer derived from 20,21-dinorebumamenin, and the isomer obtained by this process.

Application WO 89/04830, published on Jun. 1, 1989, describes new substitute derivatives of 20,21-dinoreburnamenin, the process for their preparation and their application as a medicine particularly as an antidepressant.

Depression is a pathological psychic condition combining a stressful mood change and slowing of intellectual activity and motricity. It is a morbid condition, more or less long term, characterised by a certain sadness and reduction of the energy tonicity. A bipolar depression is characterised by alternating phases: marked dejection and inertia in the first phase, euphoria and hyperactivity in the second phase.

The main symptoms used to diagnose depression in a person are depressive mood, marked reduction of interest or pleasure, problems in feeding, sleep problems, agitation or slowed psychomotricity, tiredness or loss of energy, lack of self-esteem, or an excessive feeling of culpability, a reduction of the ability to think or concentrate, or uncertainty, morbid thoughts (60% of cases) suicidal thoughts (in 15% of cases).

Causes of depression include:

1/ The Hereditary Factor

Persons whose close relatives suffer from or have suffered from depression are most likely to be affected. They have a 15% risk of developing depression, while persons whose close relatives are not depressive only have 2 to 3% risk of developing a depression.

2/ The Biochemical Factor

Current research on depression applies to neurotransmitters. It has thus been noticed that a serotonin deficiency or unbalance caused sleep loss and reduced appetite, and also that a reduction in noradrenalin has an effect on loss of energy, loss of pleasure.

3/ Environmental Factors

Children who have experienced the loss of a loved one such as their parents are more likely to develop depression later in their life. Difficulties in relations, communication problems and family, professional or other conflicts may also contribute to solitude, alienation and result in depression. Financial difficulties and other tensions can also have an important impact.

Seasonal factors must not be neglected: the depression rate is higher during months in which sunshine is lowest. Seasonal depression only occurs during the period of the year during which days are shortest, thus it occurs in winter and disappears in spring. Symptoms include tiredness, dejection, lack of vitality and loss of interest, problems with concentration and libido, sudden desire for anything sweet, an increased need for sleep or increased weight during the winter. This is what is sometimes called winter depression. 2% of all adults in central Europe are affected by seasonal depression and women are affected 4 times more frequently than men.

Depression is often accompanied by other psychological problems or it may accompany another psychological problem. Acute panic attacks and obsessions are the most frequent problems.

Schizophrenia is a chronic psychosis characterised by psychic dissociation or a discordance that disturbs the course of thought (it becomes hermetic and chaotic), it changes behaviour (which becomes strange, autistic) and upsets affectivity (archaic and paradoxical), associated with an abstract and symbolic delirium that creates themes of influence fed by auditory and cenesthesic hallucinations, and experienced in a depersonalisation atmosphere.

Maniac-depressive diseases (bipolar depression) and schizophrenia, which are two mental diseases, have the same genetic origin: the expression of various genes involved in some brain cells and in the placement of the myelin (that propagates electrical signals) would be reduced. Although these two diseases have a different clinical progress, they share some symptoms and similar medicines are often used to treat them.

Currently there are two main types of treatment for depression and schizophrenia: treatment by medicine and psychotherapies. Treatment by medicines that consists of using antidepressants, is appropriate in all forms of depression. Antidepressants act on the equilibrium of neurotransmitters. Psychotherapies are helpful for patients, but cannot be the only treatment. There are other forms of treatments such as behavioural and cognitive therapies (particularly for neurotic depression), sismotherapy or electroshock (used as a last resort).

The progress of depression is very variable and depends on many parameters: etiology, personality of the patient, etc.

If no treatment is given, it often arises that a depression can last 6 months or more, occasionally ending in the extreme termination of suicide. Up to 15% of patients with a serious depression disorder commit suicide. A relapse is observed in about 60% of all cases after treatment.

Depression may be diagnosed using the DSM IV criteria (Diagnostic and Statistical Manual of Mental Disorders, 4th edition, American Psychiatric Association Publisher; Washington D.C.)); the DSM IV is a diagnostic and statistical baseline for mental disorders, produced by the American Psychiatry Association. According to the DSM IV criteria, severe depression that is the severe and most common form of depression and for which only 10 to 25% of patients search for treatment, is characterised by one or several episodes of mood change or loss of interest for at least two weeks accompanied by at least four additional symptoms of depression; these symptoms may for example be a change in appetite, weight, sleep or psychomotricity activity; reduction of energy, a feeling of reduced self-esteem, or culpability, difficulty in thinking, concentrating, making decisions, or recurrent thoughts of death, or ideation of plans or attempts to commit suicide.

Major depressions include Treatment Resistant Depressions (TRD), and also Major Recurrent Depressive Disorders (MRDD), that are associated with hypomaniac episodes.

Classical antidepressants currently and frequently marketed belong to the following main classes: tricyclic antidepressants (TCA), monoamine oxidase inhibitors (MAO) (MAOIs), selective serotonin recapture inhibitors (SSRIs), serotonin and noradrenalin recapture inhibitors (SNDRIs), noradrenalin and selective serotonin antidepressants (NASSAs) and serotonin receptor modulators.

There is still a need for compounds capable of treating depression and/or major depression disorders in a patient who may be resistant to a treatment using the classical antidepressants mentioned above.

SUMMARY OF THE INVENTION

New derivatives of 14,15-dihydro 20,21-dinoreburnamenin14-ol have been discovered that are used to treat patients suffering from depression and related disorders. Therefore, according to a first aspect, the present invention provides a compound comprising the formula (I)

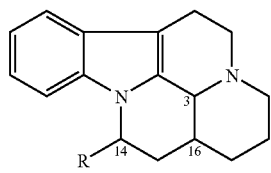

(I)

its isomers, enantiomers, diastereoisomers and mixtures thereof, wherein R represents an —AR' radical, A represents a heteroatom and R' is selected from the group consisting of
a) linear or branched $C_1$-$C_6$ alkyl radicals, $C_2$-$C_6$ alkenyl radicals and $C_2$-$C_6$ alkynyl radicals and linear or branched arylalkyl, alkoxyarylalkyl, heteroarylalkyl and heterocycloalkyl radicals,
b) esters comprising the formula —$R_1$—CO—O—$R_2$, wherein $R_1$ represents a radical selected from the group consisting of linear or branched $C_1$-$C_6$ alkylene radicals, $C_2$-$C_6$ alkenylene radicals and $C_2$-$C_6$ alkynylene radicals and $R_2$ represents a radical selected from the group consisting of hydrogen, linear or branched $C_1$-$C_6$ alkyl radicals, $C_2$-$C_6$ alkenyl radicals, $C_2$-$C_6$ alkynyl radicals and $C_3$-$C_{12}$ cycloalkyl radicals,
c) amides comprising the formula

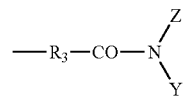

wherein $R_3$ is selected from the group consisting of linear or branched $C_1$-$C_6$ alkyl radicals, $C_2$-$C_6$ alkenylene radicals and $C_2$-$C_6$ alkynylene radicals wherein Y represents a radical selected from the group consisting of hydrogen, linear or branched $C_1$-$C_6$ alkyl radicals, $C_2$-$C_6$ alkenyl radicals and $C_2$-$C_6$ alkynyl radicals and linear or branched aryl, arylalkyl, heteroarylalkyl and heterocycloalkyl radicals, wherein Z is selected from the group consisting of hydrogen, linear or branched $C_1$-$C_6$ alkyl radicals, $C_2$-$C_6$ alkenyl radicals and $C_2$-$C_6$ alkynyl radicals and linear or branched aryl, arylalkyl, heteroarylalkyl and heterocycloalkyl radicals, provided that Y and Z together may form a $C_3$-$C_6$ cycloalkyl radical or a $C_3$-$C_6$ heterocyclic radical which can be optionally substituted by one or more $C_1$-$C_6$ alkyl, aryl, heteroaryl or halogen radicals and
d) a radical selected from the group consisting of linear or branched $C_1$-$C_6$ alkyl radicals, $C_2$-$C_6$ alkenyl radicals and $C_2$-$C_6$ alkynyl radicals, substituted by at least one amine comprising the formula

wherein Y and Z are as defined above; and pharmaceutically acceptable salts thereof.

The present invention also provides methods to prepare the compounds of the invention, pharmaceutical compositions thereof and method of use thereof.

DETAILED DESCRIPTION

Figure 1:
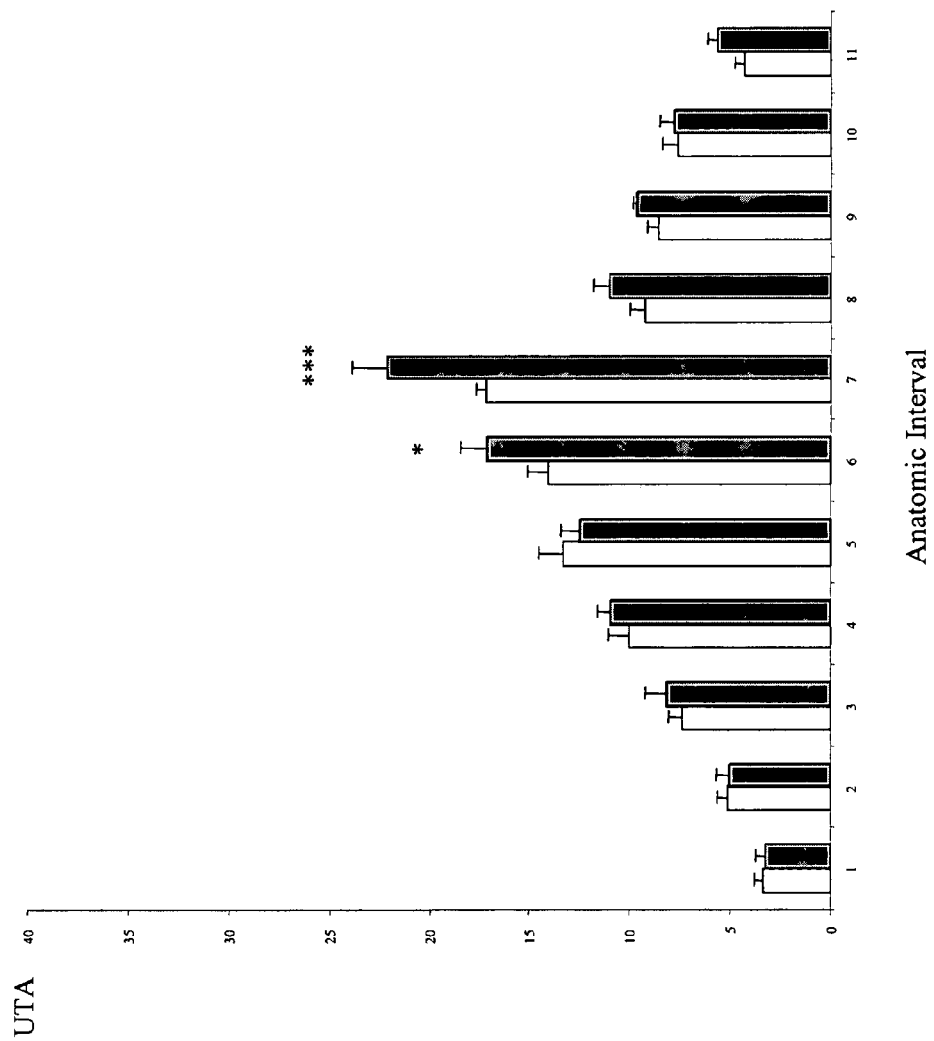
FIG. 1 represents the content of TH (Tyrosine hydroxylase) protein measured after direct transfer of frozen coronal brain sections on nitrocellulose filters, expressed in arbitrary units (UTA stands for Arbitrary Tyrosine hydroxylase Unit), in each anatomic interval (80 μm), in a group of control mice (white bars) and a group of mice treated with the compound with formula (If1) (grey bars).

The present invention provides a compound comprising the formula (I)

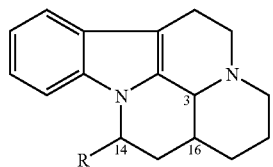
(I)

its isomers, enantiomers, diastereoisomers and mixtures thereof;
wherein R represents an —AR' radical, A represents a heteroatom and R' is selected from the group consisting of
a) linear or branched $C_1$-$C_6$ alkyl radicals, $C_2$-$C_6$ alkenyl radicals and $C_2$-$C_6$ alkynyl radicals and linear or branched arylalkyl, alkoxyarylalkyl, heteroarylalkyl and heterocycloalkyl radicals,
b) esters comprising the formula —$R_1$—CO—O—$R_2$, wherein $R_1$ represents a radical selected from the group consisting of linear or branched $C_1$-$C_6$ alkylene radicals, $C_2$-$C_6$ alkenylene radicals and $C_2$-$C_6$ alkynylene radicals and $R_2$ represents a radical selected from the group consisting of hydrogen, linear or branched $C_1$-$C_6$ alkyl radicals, $C_2$-$C_6$ alkenyl radicals, $C_2$-$C_6$ alkynyl radicals and $C_3$-$C_{12}$ cycloalkyl radicals,
c) amides comprising the formula

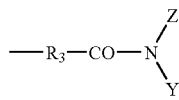

wherein $R_3$ is selected from the group consisting of linear or branched $C_1$-$C_6$ alkyl radicals, $C_2$-$C_6$ alkenylene radicals and $C_2$-$C_6$ alkynylene radicals wherein Y represents a radical selected from the group consisting of hydrogen, linear or branched $C_1$-$C_6$ alkyl radicals, $C_2$-$C_6$ alkenyl radicals and $C_2$-$C_6$ alkynyl radicals and linear or branched aryl, arylalkyl, heteroarylalkyl and heterocycloalkyl radicals, wherein Z is selected from the group consisting of hydrogen, linear or branched $C_1$-$C_6$ alkyl radicals, $C_2$-$C_6$ alkenyl radicals and $C_2$-$C_6$ alkynyl radicals and linear or branched aryl, arylalkyl, heteroarylalkyl and heterocycloalkyl radicals, provided that Y and Z together may form a $C_3$-$C_6$ cycloalkyl radical or a $C_3$-$C_6$ heterocyclic radical which can be optionally substituted by one or more $C_1$-$C_6$ alkyl, aryl, heteroaryl or halogen radicals and
d) a radical selected from the group consisting of linear or branched $C_1$-$C_6$ alkyl radicals, $C_2$-$C_6$ alkenyl radicals and $C_2$-$C_6$ alkynyl radicals, substituted by at least one amine comprising the formula

wherein Y and Z are as defined above; and pharmaceutically acceptable salts thereof.

Pharmaceutically acceptable additive salts include for example additive salts with mineral or organic acids, particularly salts formed by hydrochloric, hydrobromic, hydroiodic, nitric, sulphuric, phosphoric, acetic, formic, benzoic, maleic, fumaric, succinic, tartaric, citric, oxalic, glyoxylic, aspartic, ascorbic acids, alkylmonosulfonic acids such as methanesulfonic acid, ethane sulfonic acid, propane sulfonic acid, alkyldisulfonic acids such as methanedisulfonic acid, α,β-ethanedisulfonic acid and arylmonosulfonic acids such as benzenesulfonic acid and aryldisulfonic acids, these salts being mentioned for illustrative purposes only and not forming a limitation.

The term "alkyl" denotes hydrocarbons that can be linear or branched groups preferably with 1 to 6 carbon atoms, particularly such as methyl, ethyl, propyl, isopropyl, butyl, isobutyl, tert-butyl, pentyl, n-hexyl.

"Aryl" groups (radicals) are aromatic mono- or bicyclic hydrocarbon groups, generally with 5 to 6 chains having 5 to 10 carbon atoms. Phenyl and naphthyl radicals are examples of the aryl group. "Heteroaryl" (groups) radicals are aromatic carbonaceous groups with at least one heteroatom such as nitrogen, sulphur or oxygen on the ring(s).

The term "heterocycle" denotes aromatic mono- or bicyclic hydrocarbonaceous (groups) radicals, with at least one heteroatom such as nitrogen, sulphur or oxygen present on the ring(s). The rings may have at least one degree of unsaturation. Examples of heterocyclic radicals include particularly the piperidine, piperazine, pyrrolidine, morpholine, homopiperazine, homopiperidine, thiomorpholine, tetrahydropyridine, thiophene, furan, pyridine, pyrimidine, pyridazine and pyrazine radicals.

"Alkoxy" (groups) radicals correspond to the previously defined alkyl groups bonded to the rest of the molecule through an ether bond.

"Halogen" means an atom of fluorine, iodine, bromine or chlorine. "Heteroatom" means an atom chosen from among nitrogen, oxygen and sulphur.

"Arylalky", "heteroarylalkyl" or "heterocycloalkyl" radicals are groups including an aryl, heteroaryl or heterocycle remainder respectively, as defined above, bonded to the rest of the molecule by an alkyl chain. Benzyl and phenethyl radicals are specific examples of arylalkyl radicals.

According to one advantageous embodiment of the invention, R' represents a group with formula $R_1$—CO—O—$R_2$, in which $R_1$ represents a $C_1$-$C_6$ alkyl radical, advantageously the —$CH_2$— radical. In particular according to this variant, $R_2$ advantageously represents a hydrogen atom, a $C_1$-$C_6$ alkyl radical or a $C_3$-$C_6$ heterocyclic radical that is optionally substituted by one or more (several) $C_1$-$C_6$ alkyl radicals.

According to another advantageous embodiment of the invention, R' represents an amide with formula

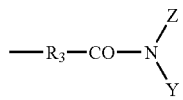

in which $R_3$ is as defined above and in which Y and Z together form a $C_3$-$C_6$ heterocyclic radical optionally substituted by one or more (several) $C_1$-$C_6$ alkyl radicals.

According to another advantageous variant of the invention, R' represents an aminoalkyl radical chosen from the group consisting of $C_1$-$C_6$ alkyl radicals that can be optionally substituted by at least one amine having the formula

in which Y and Z together form a $C_2$-$C_6$ heterocyclic radical, optionally substituted by one or more (several) $C_1$-$C_6$ alkyl radicals.

According to another advantageous variant of the invention, R' represents a heteroarylalkyl radical.

Compounds with the following formulas are particularly advantageous in the context of this invention:

(Ia)
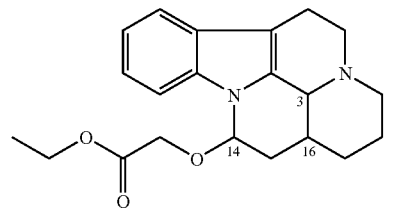

(Ib)
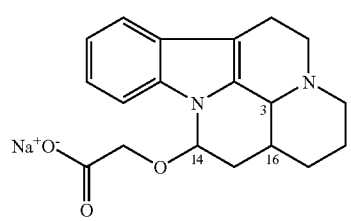

(Ic)
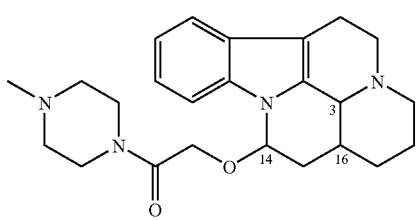

(Id)
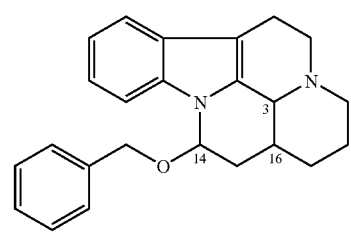

(Ie)
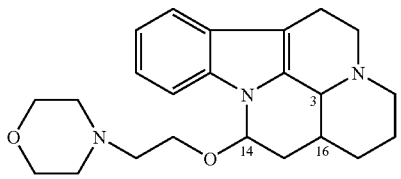

(If)
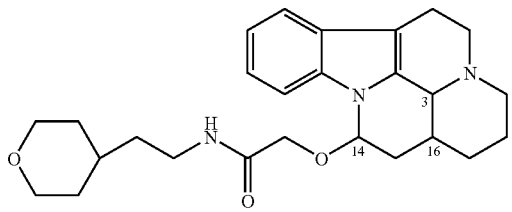

(Ig)
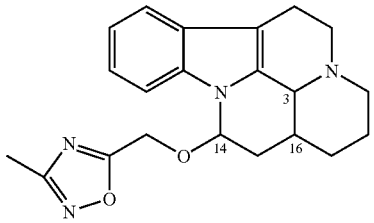

(Ih)
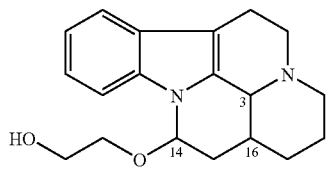

(Ii)
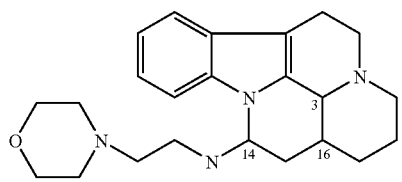

Compounds (Ia), (Id), (Ie), (If) and (Ig), and particularly compound (Ie) are preferred in the context of the invention.

The compound with formula (I) is characterised by two enantiomeric forms 3α and 16α, and if applicable is characterised for each of these enantiomers by a pair of diastereoisomers according to the carbon 14 configuration: the ((3α, 14α) and (3α, 14β)) pair and the ((14α, 16α) and (14β, 16α)) pair.

In compounds with formula (I), the hydrogen atom in position 3 and the hydrogen atom in position 16 are advantageously in the trans position, and the radical R in position 14 may possibly be in α or β form (the terms α and β refer to the substituent and not to hydrogen, in accordance with the convention for naming steroid derivatives).

In the context of this invention, form 3α corresponds to formulas (I) in which the carbon in position 3 is in the S configuration and the carbon in position 16 is in the R configuration. In the context of this invention, the 16α form corresponds to formulas (I) in which the carbon in position 3 is in the R configuration and the carbon in position 16 is in the S configuration.

Therefore, the purpose of one particular aspect of the invention is a compound with formula (I) or one of its pharmaceutically acceptable salts, in which the compound with formula (I) or one of its pharmaceutically acceptable salts is in the form of a racemic or optically active mixture.

The compound with formula (I) or one of its pharmaceutically acceptable salts is advantageously chosen from the following compounds with formula (I):

a) compounds in the dextrorotatory and/or levorotatory form (3α); and b) compounds in the dextrorotatory and/or levorotatory form (16α), and in which the mixture of the two levorotatory and dextrorotatory diastereoisomers present in compounds a) and b) may or may not be in an equimolar proportion.

According to one advantageous variant of the invention, the compound with formula (I) or one of its pharmaceutically acceptable salts is advantageously chosen from among compounds with the following formulas (I):

a) compounds in the dextrorotatory and/or levorotatory form (3α, 14α);

b) compounds in the dextrorotatory and/or levorotatory form (3α, 14β);

c) compounds in the dextrorotatory and/or levorotatory form (14α, 16α); and d) compounds in the dextrorotatory and/or levorotatory form (14β, 16α).

In the context of this invention, a "trans epimer" means an epimer in which the hydrogen atoms carried by carbons 3 and 16 are always in the trans position and the R substitute is in the trans position with respect to the hydrogen atom carried by carbon 16. In the context of this invention, the term "cis epimer" will be used to mean the epimer in which hydrogen atoms carried by carbon 3 and carbon 16 are always in the trans position and the substitute R is in the cis position with respect to the hydrogen atom carried by carbon 16.

According to one advantageous variant of the invention, compounds with formula (I) or one of their pharmaceutically acceptable salts represent the epimer obtained in majority during synthesis, which may be the trans epimer or the cis epimer.

In one preferred embodiment of the invention, the compound corresponds to the epimer (Ie1) composed of the (3α, 14β) and (16α, 14α) pair of enantiomers with the following formulas:

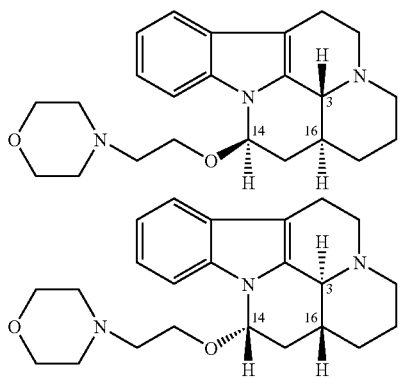

It will be seen that in this epimer (Ie1), the substitute carried by the carbon 14 atom, in this case ethylmorpholino, is always in the trans position with respect to the hydrogen carried by the carbon atom 16, the hydrogen atoms carried by carbon 3 and carbon 16 always being trans. More particularly, the preferred compound is the enantiomer obtained second (Ie1b) (second eluted compound) at the column output when HPLC (High Performance Liquid Chromatography) is done on the epimer (Ie1) ((3α, 14β) and (16α, 14α) pair) using a column in which the stationary phase is composed of silica gel particles (particle size 5 μm), on which tris (2,5-dimethylphenylcarbamate) cellulose is grafted, the mobile phase used being acetonitrile.

We will now describe the compound in which the radical R of the compound (I) represents a hydrogen atom with a double bond between the carbon 14 and carbon 15 satisfying the following formula (Ij):

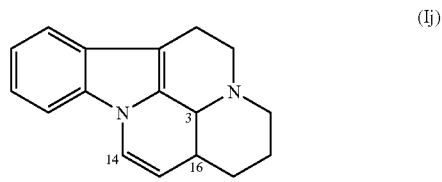

for use as a medicine. Compound (Ij) is obtained particularly by dehydratation of compounds with formula (I), in which the radical R represents the radical —AR' as defined above.

In particular, we will describe the compound (Ij1) in this document that comprises the following two enantiomers:

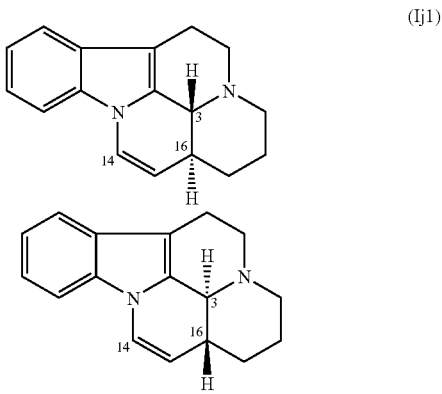

The purpose of the second aspect of the invention is a compound with formula (I) according to the invention for use as a drug, and a pharmaceutical composition comprising a compound according to the invention and a pharmaceutically acceptable excipient.

In particular, the purpose of this invention is the use of a compound with formula (I) according to the invention or a composition according to the invention, for the preparation of a pharmaceutical composition intended for the treatment and/or prevention of depression.

In particular, the purpose of this invention is the use of a compound or a composition according to the invention, the radical R of the compound (I) possibly also representing a hydrogen atom with a double bond between carbon 14 and carbon 15 (compound of formula (Ij) particularly Ij1) for the preparation of a pharmaceutical composition intended for the treatment and/or prevention of major depressive disorders (MDD) (Ref. 14, 15, 16).

Compounds according to the invention are more efficient antidepressants and have faster action than classical antidepressants.

According to another particular aspect, the use of a compound or a composition according to the invention, the radical R of the compound (I) also possibly representing a hydrogen atom with a double bond between carbon 14 and carbon 15, is intended for the treatment or prevention for patients suffering from depression and who are partially or totally resistant to treatment by classical antidepressants (patients suffering from TRD), such as antidepressants belonging to the class consisting of tricyclic antidepressants (TCA), monoamine oxidase inhibitors (MAOIs), selective serotonin recapture inhibitors (SSRIs), serotonin and noradrenalin recapture inhibitors (SNDRIs), noradrenalin and selective serotonin antidepressants (NASSAs) or serotonin receptor modulators.

According to another particular aspect, the use of a compound or a composition according to the invention, the radical R of the compound (I) also possibly representing a hydrogen atom with a double bond between carbon 14 and carbon 15, is intended to make patients resistant to classical anti-depressant treatments and suffering from depression, particularly severe depression, more sensitive to these treatments.

According to another particular aspect, the use of a compound or a composition according to the invention, the radical R of the compound (I) also possibly representing a hydrogen atom with a double bond between carbon 14 and carbon 15, is intended for the treatment and/or prevention of a bipolar type major depression according to the DSM IV, particularly a major recurrent depressive disorder (MRDD).

According to another particular aspect, the use of a compound or a composition according to the invention, the radical R of the compound (I) also possibly representing a hydrogen atom with a double bond between carbon 14 and carbon 15, is intended for the treatment and/or prevention of depression with severity evaluated with a score of more than 26 using the HAMD ("Hamilton Depression Scale") scale, or with a score of more than 35 on the MADRS (Montgomery and Asberg Depression Rating Scale) scale.

According to another particular aspect, the use of a compound or a composition according to the invention, the radical R of the compound (I) also possibly representing a hydrogen atom with a double bond between carbon 14 and carbon 15, is intended for the treatment and/or prevention of schizophrenia.

Thus, compounds according to the invention in which the radical R of the compound (I) can also represent a hydrogen atom with a double bond between carbon 14 and carbon 15, can be used in the treatment and/or prevention of bipolar depression and/or schizophrenia, particularly for normalisation of negative symptoms of bipolar depression (Ref. 17) and schizophrenia (Ref. 18).

Considering that compound tests on Balb/c mice according to the invention, have shown that these compounds are capable of: 1) restoring the noradrenergic phenotype in a significant population of the locus caeruleus; 2) restoring noradrenergic innervation in the prefrontal cortex; 3) restoring the hypocretin phenotype in a subpopulation of hypothalamus neurones; and 4) inverting the incapacity of these mice with consanguine race to have an increase in REM sleep after being deprived of sleep; according to a new aspect, the invention also relates to use of the compounds, in which the radical R of the compound (1) can also represent a hydrogen atom with a double bond between carbon 14 and carbon 15, for making a drug or for the preparation of a pharmaceutical composition intended for prevention and/or treatment of wakening-sleep cycle disorders. The wakening-sleep cycle disorders are chosen particularly among the group composed of narcolepsy, hypersomnia and a chronic condition of hypo arousal.

According to a new aspect, the purpose of this invention is the use of a compound with formula (I) according to the invention or a composition according to the invention, the radical R of compound (I) can also represent a hydrogen atom with a double bond between carbon 14 and carbon 15, for the preparation of a pharmaceutical composition intended for the treatment and/or prevention for the treatment of cognitive components of symptomatic frontal disorders (Mild Cognitive Impairment (Ref. 18), such as pre-dementia and dementia conditions related to Alzheimer's disease or Parkinson's disease (Ref. 12)) or behavioural problems: hypoactivity, attention problems, characterial problems (of the Attention Deficit—Hyperactivity (ADHD) type reference 21). Thus, according to this new aspect, the purpose of this invention is this use in which cognitive components of symptomatic frontal problems are chosen from among pre-dementia and dementia states related to Alzheimer's disease and Parkinson's disease, or behavioural diseases chosen from among attention problems and characterial problems.

According to another particular aspect, the purpose of the invention is the use of a compound with formula (I) according to the invention or a composition according to the invention, the radical R of the compound (I) possibly also representing a hydrogen atom with a double bond between carbon 14 and carbon 15 for the preparation of a pharmaceutical composition to be used for the treatment and/or prevention of memory problems, related particularly to aging or to Alzheimer's disease or Parkinson's disease.

More particularly, the purpose of the invention is the use of a compound with formula (I) or one of its pharmaceutically acceptable salts according to this invention, for use as a drug that can be administrated orally, intravenously, or by an intraperitoneal or intramuscular route, or by any other route which permits to obtain an antidepressive effect according to this invention, or making patients suffering from major depression who were resistant to classical antidepressant treatments, sensitive to these treatments, or to obtain the required prevention or treatment in the previous uses.

Active substances of drugs or pharmaceutical compositions according to the invention may be in any of the oral galenical forms normally used including tablets, capsules and liquid preparations such as elixirs and suspensions containing various colour, taste and stabilisation masking substances.

To produce oral galenical forms according to the invention, the active substance may be mixed with various conventional materials such as starch, calcium carbonate, lactose, sucrose and dibasic calcium phosphate to facilitate the encapsulation process. Magnesium stearate as an additive, provides a useful lubrication function if necessary.

Active substances of pharmaceutical compositions according to the invention may be dissolved or present in suspension in a pharmaceutically acceptable sterile liquid such as sterile water, a sterile organic solvent or a mixture of these two liquids. Preferably, such a liquid is appropriate for parenteral injection.

When the active substance is sufficiently soluble, it can be dissolved in a normal saline solution such as a pharmaceutically acceptable sterile liquid; if it is not sufficiently soluble, it can be dissolved in aqueous solutions of an appropriate organic solvent, for example propylene glycol or polyethylene glycol. Aqueous propylene glycol containing 10 to 75% by weight of glycol is usually appropriate. In other examples, other compositions can be obtained by dispersing the active substance as a very fine concentrate in an aqueous carboxymethylic solution of starch cellulose or sodium, or in an appropriate oil, for example peanut oil.

Liquid pharmaceutical compositions such as sterile solutions or suspensions can be used for intramuscular, intraperitoneal or subcutaneous injections.

Preferably, the pharmaceutical composition is in the form of unit doses, for example such as tablets or capsules. In this form, the composition is subdivided into unit doses containing appropriate quantities of active substance; unit doses may be packaged compositions, for example powders, flasks or phials. The quantity of active substance in a unit dose of the composition may be modified or adjusted by 2 mg or less, or by 50 mg or more, depending on the particular need and the activity of the active substance.

The recommended oral dose of compounds with formula (I) for man may be from 20 to 60 mg/day and this dose may be administered in two or three separate doses, preferably during a meal. Most resistant melancholic patients respond to a dose of 20 mg/day, but 40 mg or even 60 mg may be necessary.

Those skilled in the art also are aware that methods of administrating compounds according to this invention can change significantly. Apart from other oral administrations, slow release compositions may be preferred. Other administration methods may include but are not limited to intravenous injections, intramuscular and intraperitoneal injections, subcutaneous implants, and mouth, sublingual, transdermal, topic, rectal and intranasal administration.

According to one particular embodiment, the purpose of the invention is compounds with formula (I) or their pharmaceutically acceptable salts according to the invention, for use as a medicine at daily doses of 20 to 60 mg in the adult.

A person trained to treat persons with the ailments discussed herein will be able to determine the appropriate dose for each patient; this dose may vary as a function of the age, weight and response to treatment of a given patient. The dose examples given above are representative of the average. However, doses smaller or larger than this average may be administered.

Process for preparation of compounds with formula (I): according to the invention, compounds such as those defined by the formula (1) may be prepared from 14,15 dihydro-20, 21-dinoreburnamenin14-ol by the following processes.

1) Preparation of 14,15 dihydro-20,21-dinorebumamenin14-ol:

The 14,15 dihydro-20,21-dinoreburnamenin14-ol compound is prepared by treatment of optically active compounds with formula (II) or (II').

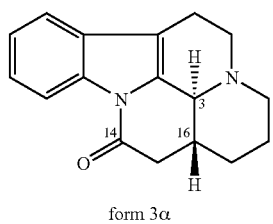

form 3α
(II)

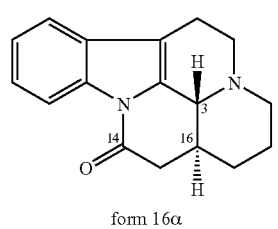

form 16α
(II')

using a reducing agent; the result obtained is two pairs of diastereoisomers [(3α, 14α), (3α, 14β)] and [(14α, 16α), (14β, 16α)] of 14,15 dihydro-20,21-dinoreburnamenin 14-ol, or a mixture of them, and if required the reaction product is treated by a mineral or organic acid to form a salt from the product.

Products with formula (II) and (II') can be prepared for example as described in French patent application under number FR 2 190 113. The racemic mixture of compounds with formula (II) may be separated by split.

One of the two enantiomers with formula (II) can be reduced to obtain a pair of diastereoisomers (±) of 14,15 dihydro-20,21-dinoreburnamenin14-ol or mixtures of them in very variable proportions of the two diastereoisomers. The experiment described in French patent application published under number FR 2 623 503 shows that in practice only one of the two diastereoisomers is obtained (see example B).

Used compounds with formula (II) may be in racemic or optically active form. Reduction compounds of 14,15 dihydro-20,21-dinoreburnamenin14-ol obtained from the product with formula (II) are obviously obtained in the corresponding stereochemical form.

Compounds with formula (II) may be used in the form of one of their additive salts with mineral or organic acids. If this is the case, the products of 14,15-dihydro-20,21-dinoreburnamenin14-ol may be obtained in salified or non-salified form depending on the chosen operating conditions.

Racemic or optically active mixtures of compounds of 14,15 dihydro-20,21-dinorebumamenin14-ol may also be prepared as indicated in French patent application published under number FR 2381 048 and in the French additional certificate application under number FR 2 433 528.

In the preferred embodiments of the invention, the process described above is made as follows.

The reducing agent used may be a hydride, particularly a mixed hydride for example such as mixed lithium and aluminium hydride, sodium and aluminium diethylhydride, sodium hydroboride, lithium hydroboride, diisobutyl-aluminium hydride. The reduction reaction is carried out within an organic solvent or a mixture of solvents, for example such as an ether like ethylic ether, tetrahydrofuran, or an aromatic hydrocarbon such as toluene, benzene, xylene. The reduction reaction may be carried out at a temperature varying from −20° C. to the reflux temperature of the reaction medium. It is advantageously performed at ambient temperature. In the case in which a metal hydride is used as the reducing agent, 14,15 dihydro-20,21-dinoreburnamenin 14-ol is released from the intermediate complex formed with the hydride, according to current practice, by the addition of an aqueous alkaline solution, for example such as a solution of sodium hydroxide.

Reduction of compound (II) trans 3α leads to the compound (+) (3α, 14α) 14,15-dihydro 20,21-dinoreburnamenin14-ol. Reduction of compound (II') trans 16α can lead to the compound (−) (14β, 16α) 14,15-dihydro 20,21-dinoreburnamenin14-ol.

Figure 2:
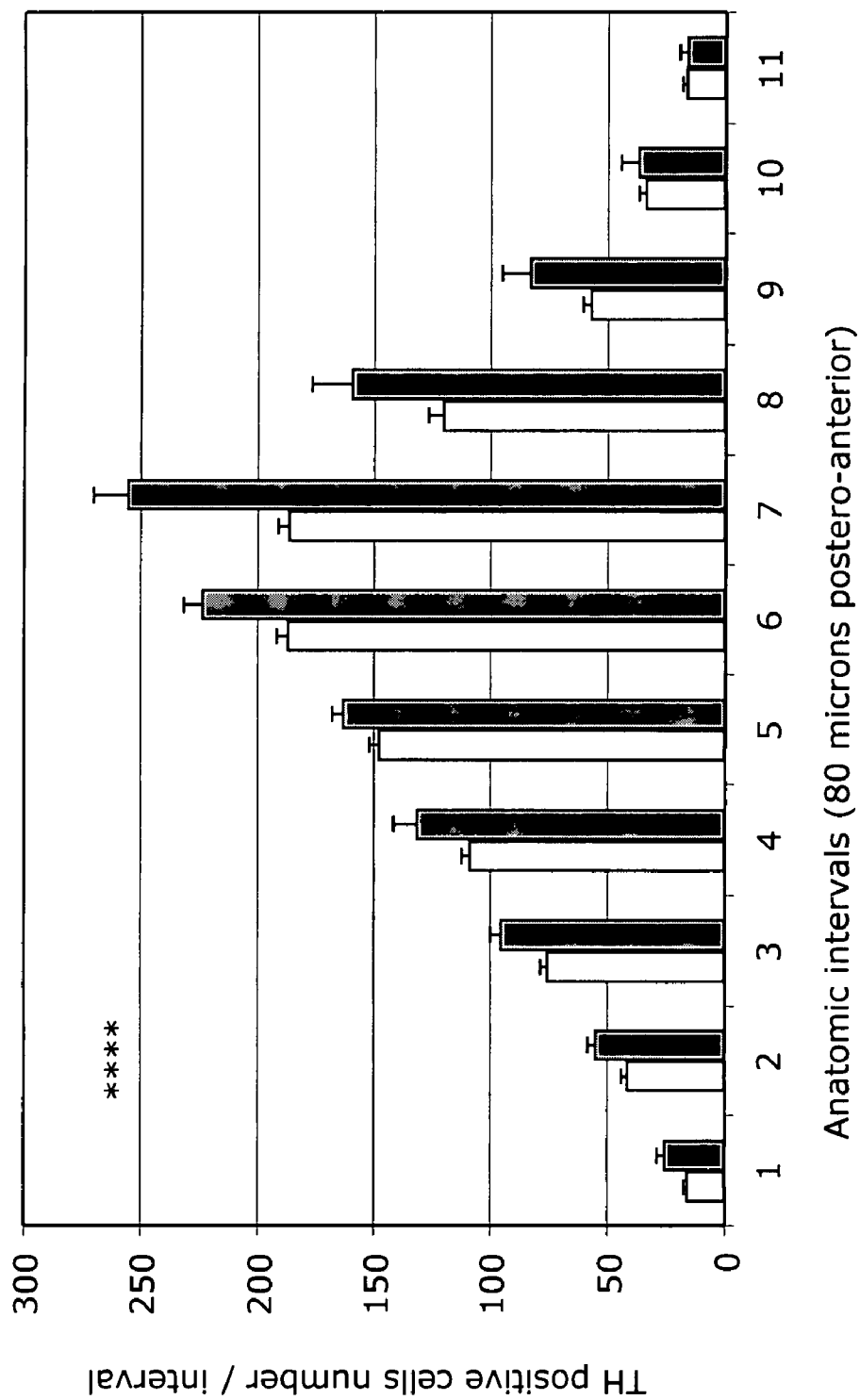
FIG. 2 provides posterior-anterior distribution of the number of cells containing TH in the LC determined by immunohistochemistry in a control group of Balb/c mice (white bars) and in a group of mice treated by the molecule with formula (Ie1) (grey bars).

These compounds can be treated by an acid, for example hydrochloric acid to obtain the (−) (3α, 14β) 14,15-dihydro 20,21-dinoreburnamenin14-ol and (+) (14α, 16α) 14,15-dihydro 20,21-dinoreburnamenin14-ol majority forms respectively (see following diagram and FIG. 2).

Diagram representing the general method for synthesizing optically active isomers of compounds of 14,15 dihydro-20, 21-dinorebumamenin14-ol from compounds with formula (II) (compounds with formula (II) described in the Belgian patent application published as No. BE 764 166)

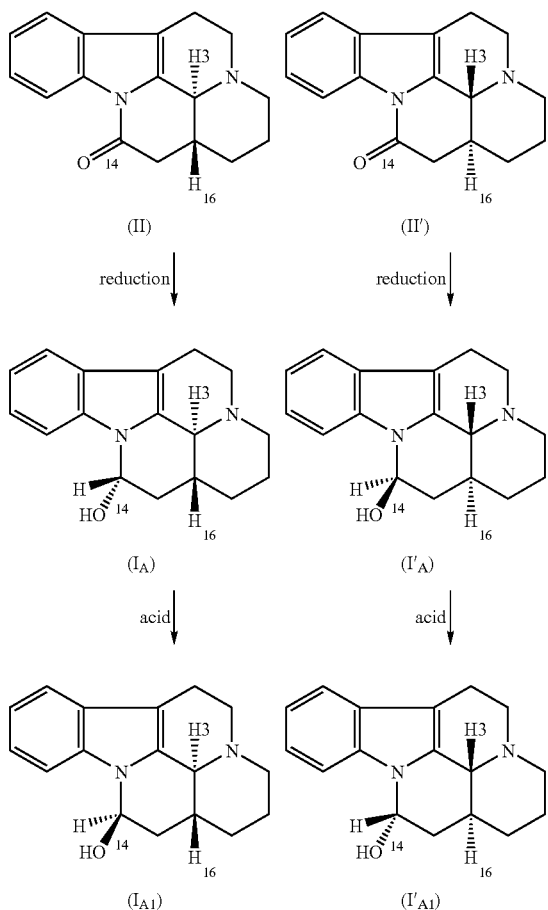

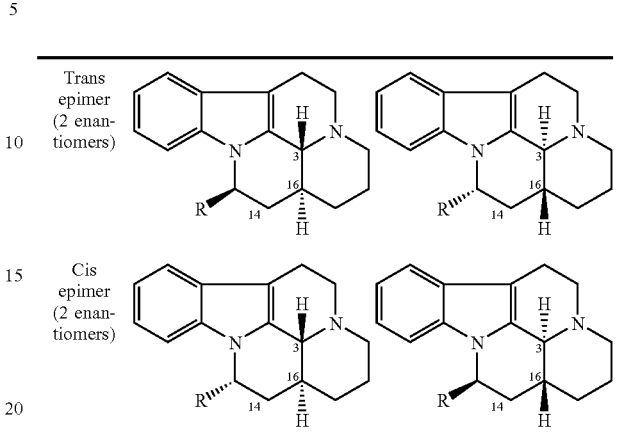

There are two enantiomers for each epimer, as a function of the position (in the foreground or in the background) of the hydrogen atoms in position 3 and 6 (these hydrogen atoms are always trans).

In the examples 1 to 9 given below, the expression "2 epimers" means that the compound (initial or synthesised compound) is in the form of a mixture of two epimers (four diastereoisomers) and the expression "1 epimer" means that the compound (initial or synthesised) is in the form of a single epimer (two enantiomers), the cis epimer or the trans epimer.

EXAMPLE 1

Process for Preparation of the Compound with Formula (Ia): (±) (16α) 14,15-dihydro 14-ethoxycarbonylmethoxy-20,21-dinoreburnamenin

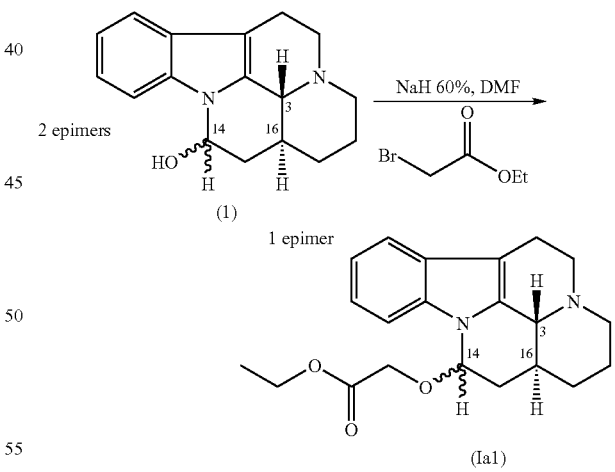

One of the diastereoisomers, or a mixture of the diastereoisomers, may be isolated by the usual methods: chromatography, direct crystallisation, differential solubilization for example such as differential solubilization in hot toluene.

2) Preparation of Compounds with Formula (I):

Compounds according to the invention can be prepared from 14,15 dihydro-20,21-dinorebumamenin14-ol by O-alkylation or N-alkylation in the presence of a strong base such as NaH, or from previously synthesised compounds according to the invention.

The examples and the Figures described below are intended to illustrate the invention without in any way limiting its scope.

In examples 1 to 9 given below:

the hydrogen atom in position 3 and the hydrogen atom in position 16 are trans (the bond can be (3β, 16α) or (3α, 16β))

in position 14, the terms α and β refer to the substitute and not to hydrogen.

Moreover, the compounds synthesised in examples 1 to 9 given below may be in the form of a mixture of two epimers (in other words four diastereoisomers) or a single epimer, the cis epimer or the trans epimer (in other words two enantiomers). The two epimers are defined as a function of the position (in the foreground or background) of the —R radical carried by the carbon atom in position 14 and as a function of its position with respect to the hydrogen carried by carbon 16.

50 mg (0.19 mmol) of compound (1) is dissolved in 4 ml of anhydrous dimethylformamide (DMF), and then 19 mg of 60% NaH (1.2 eq) is added. Once the gaseous release is terminated, 25 μl (1.2 eq) of ethyl bromoacetate is added and it is stirred at ambient temperature for one night. The reaction medium is then concentrated, and the residue is dissolved with dichloromethane (CH$_2$Cl$_2$). The organic phase is washed with water. It is dried on magnesium sulphate (MgSO$_4$), filtered and evaporated until dry. Purification is done on an eluted silica column with a CH$_2$Cl$_2$/

MeOH 99:1 then CH$_2$Cl$_2$/MeOH 98:2 mixture. Compound (Ia) is obtained in the form of 2 epimers: 28 mg of off-white powder (Ia1) and 3 mg of a yellow sticky solid (Ia2). Yield: 46% (42% of Ia1 and 4% of Ia2). Melting point=105° C.-108° C.

RMN $^1$H CDCl$_3$ (300 MHz) δ (ppm): 1.25 (m, 2H, —CH$_2$); 1.27 (t, 3H, —CH$_2$CH$_3$); 1.79 (m, 2H, —CH$_2$); 2.33 (m, 4H, 2 —CH$_2$); 2.72 (m, 3H, —H$_2$, —CH); 3.12 (m, 3H, —CH$_2$, —CH); 4.11 (m, AB system, 2H, —COCH$_2$, J=15.9 Hz); 4.22 (q, 2H, —CH$_2$CH$_3$); 5.77 (m, 1H, CHOH); 7.15 (m, aromatic 2H, H); 7.45 (dd, 1H, aromatic H, J=7.22 Hz, J=1.55 Hz); 7.68 (dd, 1H, aromatic H, J=7.03 Hz, J=1.69 Hz).

EXAMPLE 2

Process for Preparation of Compound with Formula (Ib1): sodium; (±) (3β, 16α) 14,15-dihydro 14-carboxymethoxy 20,21 dinoreburnamenin

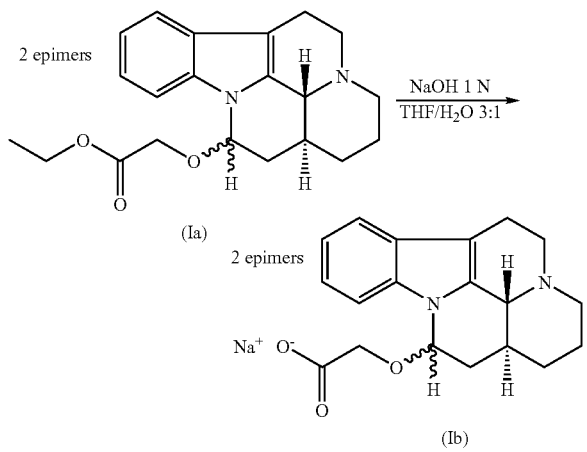

182 mg (0.51 mmol) of compound (Ia) is dissolved in 8 ml of a mixture of tetrahydrofuran (THF)/H$_2$O 3:1. 485 μl (0.95 eq) of a 1N soda solution is added. It is stirred for one night at ambient temperature. The THF is concentrated, dissolved with CH$_2$Cl$_2$ and water. The aqueous phase is washed three times with CH$_2$Cl$_2$. The aqueous phase is concentrated and the solid obtained is dried. The result is 160 mg of the required compound in the form of a yellow solid. Yield: 90% Melting point=200° C.

RMN $^1$H MeOD (300 MHz) δ (ppm): 1.31 (m, 1H, —CH); 1.59 (m, 1H, —CH); 1.87 (m, 4H, 2 —CH$_2$); 2.41 (m, 2H, —CH$_2$); 2.71 (m, 2H, —CH$_2$); 2.93 (m, 3H, —CH$_2$, —CH); 3.13 (m, 1H, —CH); 3.92 (m, AB system, 2H, —COCH$_2$, J=15 Hz); 5.70 (m, 1H, CHOH); 7.07 (m, aromatic 2H, H); 7.39 (d, 1H, aromatic H, J=7.1 Hz); 7.70 (d, 1H, aromatic H, J=7.9 Hz).

EXAMPLE 3

Process for Preparation of Compound with Formula (Ic1): (±) (3β, 16α) 14,15-dihydro 14-[2-(N-methyl-piperazin-1-yl)-2-oxo-ethoxy]20,21-dinoreburnamenin

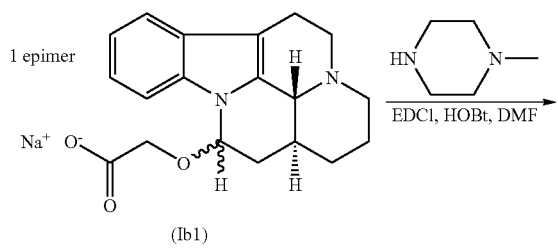

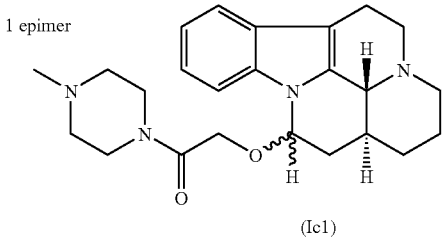

(Ib1): Majority Epimer Separated After Synthesis of Compound (Ib).

80 mg (0.23 mmol) of compound (Ib1) is dissolved in 5 ml of DMF. 31 μl (1.2 aq) of N-methylpiperazine, 53 mg (1.2 eq) of 1-(3-dimethylaminopropyl-3-ethylcarbodiimide hydrochlorate (EDCl.HCl) and 37 mg (1.2 eq) of 1-hydroxybenzotriazole hydrate (HOBt.H$_2$O) are added. It is stirred for 48 h at ambient temperature, and the reaction mixture is concentrated. The residue is dissolved with CH$_2$Cl$_2$, the organic phase is washed with a saturated solution of NaHCO$_3$. It is dried on MgSO$_4$, and filtered and concentrated. The yellow oil obtained is purified on an eluted silica column with a CH$_2$Cl$_2$/MeOH 95:5 then a CH$_2$Cl$_2$/MeOH 90:10 mixture. The result is 50 mg of a sticky yellow powder (Ic1). Yield: 53% Melting point=44° C.-48° C.

RMN $^1$H CDCl$_3$ (300 MHz) δ (ppm): 1.26 (m, 1H, —CH); 1.60 (m, 1H, —CH); 1.82 (m, 4H, 2 —CH$_2$); 2.34 (m, 6H, 3 —CH$_2$); 2.42 (m, 3H, —CH$_2$, —CH); 2.75 (m, 3H, —CH$_2$, —CH); 3.04 (m, 3H, —CH$_2$, —CH); 3.42 (m, 2H, —CH$_2$); 3.60 (m, 2H, —CH$_2$); 4.19 (m, AB system, 2H, —COCH$_2$, J=13.5 Hz); 5.78 (m, 1H, CHOH); 7.12 (m, aromatic 2H, H); 7.44 (d, 1H, H aromatic); 7.55 (d, 1H, H aromatic).

EXAMPLE 4

Synthesis of Compound (Id): (±) (3β, 16α) 14,15-dihydro 14-benzyloxy 20,21-dinoreburnamenin

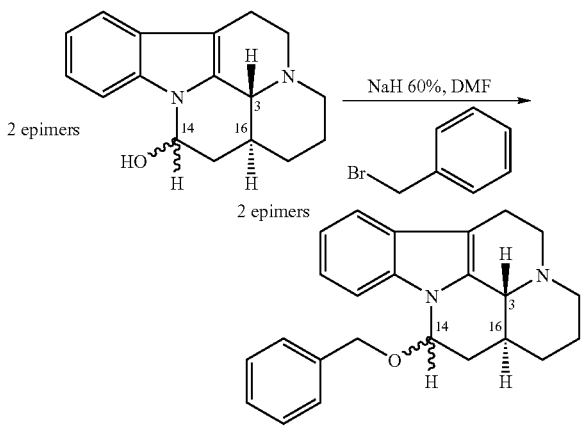

The same method is used as for the synthesis of compound (Ia) (example 1) using benzyl bromide instead of ethyl bromoacetate. Yield 52% (Id) (the two epimers were not separated). Melting point 112° C.-115° C.

RMN $^1$H (300 MHz, CDCl$_3$) δ (ppm) 1.15-1.35 (m, 2H); 1.78-2.02 (m, 4H); 2.18-2.40 (m, 2H); 2.54-2.89 (m, 3H); 2.94-3.21 (m, 3H); 4.48-4.73 (m, 2H); 5.74 (m, 1H); 7.13 (m, 2H); 7.18-7.38 (m, 5H); 7.45 (m, 1H); 7.54 (m, 1H).

EXAMPLE 5

Synthesis of Compound (Ig): (±) (3β, 16α) 14,15-dihydro 14-(3-methyl-[1,2,4]oxadiazol-5-yl-methoxy) 20,21-dinoreburnamenin

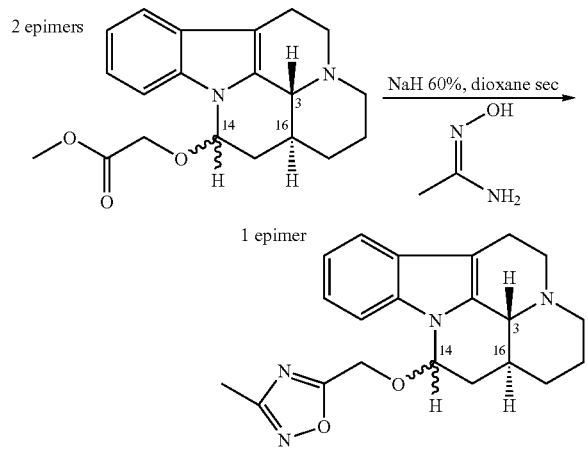

The initial methyl ester was synthesised using the same method as was used for the synthesis of compound (Ia) using methyl bromoacetate instead of ethyl bromoacetate.

209 mg (2.82 mmol) of oxime acetamide and 113 mg (2.82 mmol) of 60% NaH are dissolved in 10 mL of anhydrous diethylene dioxide. A molecular sieve spatula is added and the reaction mixture is heated to 65° C. for one hour. 320 mg (0.94 mmol) of methyl ester dissolved in 10 mL of anhydrous diethylene dioxide is added at this temperature, and the reaction mixture is heated to 75° C. for one night. The reaction mixture is concentrated, the residue is dissolved with an unsaturated solution of NaHCO₃, and it is triturated and filtered. The yellow solid obtained is purified on an eluted silica column with a CH₂Cl₂/MeOH mixture (99:1). The two epimers are separated. 79 mg of majority epimer (Ig1) is obtained in the form of a white powder.

Yield: 23% for the majority epimer, the minority epimer was not isolated. Melting point: 124° C.-125° C. RMN ¹H (300 MHz, CDCl₃) δ (ppm): 1.21-1.38 (m, 1H); 1.60-1.73 (m, 1H); 1.75-2.03 (m, 4H); 2.29-2.55 (m, 5H); 2.65-2.96 (m, 3H); 2.98-3.23 (m, 3H); 4.68 (d, 1H, J=14.1 Hz); 4.80 (d, 1H, J=14.1 Hz); 5.83 (m, 1H); 7.16 (m, 2H); 7.46 (m, 1H); 7.59 (m, 1H).

EXAMPLE 6

Synthesis of Compound (Ih): (±) (3β, 16α) 14,15-dihydro 14-(2-hydroxy-ethoxy) 20,21-dinoreburnamenin

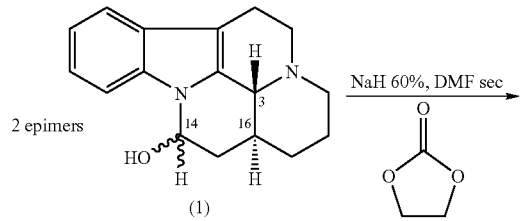

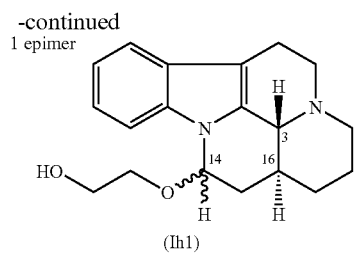

300 mg (1.12 mmol) of compound (1) is put into suspension in 10 ml of anhydrous DMF and 54 mg (1.2 eq) of 60% NaH is then added. 492 mg (5.0 eq) of ethylene carbonate is added and the reaction mixture is heated to 110° C. for one hour and then 80° C. for four hours. The reaction mixture is concentrated, and the residue is dissolved with CH₂Cl₂. The organic phase is washed twice with water and once with a saturated solution of NaHCO₃. It is dried on MgSO₄, filtered and concentrated. The brown oil obtained is purified on an eluted silica column with a CH₂Cl₂/MeOH mixture (99:1) then a CH₂Cl₂/MeOH mixture (98:2) then a CH₂Cl₂/MeOH mixture (96:4).

The compound is obtained in the form of 2 epimers: 111 mg (Ih1) of beige solid and 100 mg of beige solid (Ih2). Yield 61% (32% of (Ih1) and 29% of the other epimer).

RMN ¹H (400 MHz, CDCl₃) δ (ppm): 1.22-1.38 (m, 1H); 1.78-2.18 (m, 6H); 2.21-2.41 (m, 2H); 2.61 (m, 1H); 2.71-2.85 (m, 2H); 2.97-3.20 (m, 3H); 3.56-3.82 (m, 4H); 5.61 (m, 1H); 7.14 (m, 2H); 7.44 (m, 1H); 7.52 (m, 1H).

Melting point: 129° C.-132° C.

EXAMPLE 7

Synthesis of Compound (Ie)

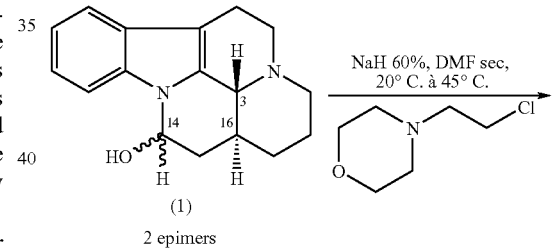

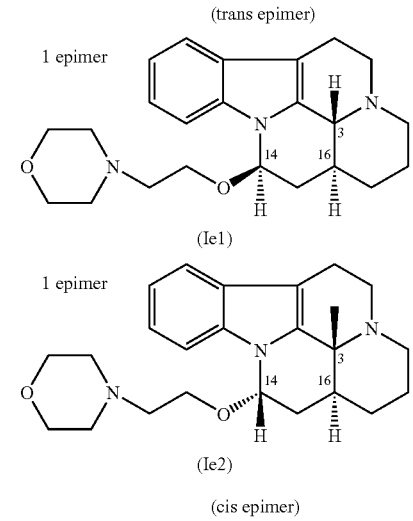

a) Synthesis of 4-(2-chloroethyl)-morpholine 5.0 g (26.9 mmole) of hydrochlorate of 4-(2-chloroethyl-morpholin) is dissolved in 16 mL of distilled water. Potassium carbonate ($K_2CO_3$) is added in 15 g portions. The aqueous solution is extracted five times with ethyl acetate (AcOEt). Drying is done on $MgSO_4$, and the organic phase is filtered and concentrated.

The result obtained is 3.37 g of 4-2(chloroethylmorpholine) in the form of a clear yellow oil.

Yield: 84%.

b) Synthesis of Compounds (Ie): (±) (3β, 14β, 16α) 14,15-dihydro 14-(2-morpholin-4-yl-ethoxy) 20,21-dinoreburnamenin and (±) (3β, 14α, 16α) 14,15-dihydro 14-(2-morpholin-4-yl-ethoxy) 20,21-dinoreburnamenin 500 mg (1.86 mmol) of compound (1) is put into suspension in 20 mL of anhydrous DMF. 90 mg (1.2 eq) of 60% NaH is added and stirred for 45 minutes at ambient temperature. 558 mg (2.0 eq) of 4-(2-chloroethyl) morpholine dissolved in 10 mL of anhydrous DMF is added followed by 140 mg (0.5 eq) of sodium iodide. It is stirred for 8 hours at 45° C. and then 90 mg (1.2 eq) of 60% NaH, 558 mg (2.0 eq) of 4-(2-chloroethyl) morpholine dissolved in 2 ml of anhydrous DMF and 280 mg (1.0 eq) of sodium iodide are added, at the same temperature. Heating is continued for 18 hours and then 90 mg (1.2 eq) of 60% NaH, 558 mg (2.0 eq) of 4-(2-chloroethyl) morpholine dissolved in 2 mL of anhydrous DMF and 280 mg (1.0 eq) of sodium iodide are added again. Stirring is continued for 24 h at 45° C. The reaction mixture is concentrated, and the residue is dissolved with $CH_2Cl_2$. The organic phase is washed three times with water. It is dried on $MgSO_4$, filtered and concentrated. The residue obtained is dissolved with $Et_2O$, the insoluble material is filtered and the filtrate is concentrated. The brown oil obtained is purified on an eluted silica column with a $CH_2Cl_2/MeOH/NH_2OH$ (99:0.5:0.5) mixture.

Two epimers are obtained: 340 mg of sticky yellow solid (Ie1) and 29 mg (Ie2) of a yellow solid. Yield: 52% (48% of (Ie1) and 4% of (Ie2))

(Ie1):

RMN $^1$H (300 MHz, $CDCl_3$) δ (ppm) 0.86 (m, 1H); 1.18-1.40 (m, 1H); 1.78-1.92 (m, 4H); 2.21-2.41 (m, 2H); 2.48-2.92 (m, 9H); 2.98-3.15 (m, 3H); 3.59 (m, 1H); 3.70-3.92 (m, 5H); 5.62 (m, 1H); 7.08-7.21 (m, 2H); 7.44 (m, 1H); 7.63 (m, 1H).

Melting point: 116° C.-118° C.

(Ie2):

RMN $^1$H (300 MHz, $CDCl_3$) δ (ppm) 1.12-1.32 (m, 1H); 1.79-2.82 (m, 16H); 2.95-3.21 (m, 3H); 3.43-3.80 (m, 6H); 5.69 (bs, 1H); 7.11 (m, 2H); 7.34-7.52 (m, 2H).

Melting point: 91° C.-93° C.

c) Separation of Two Enantiomers (Ie1a) and (Ie1b) by Preparative Chiracel HPLC

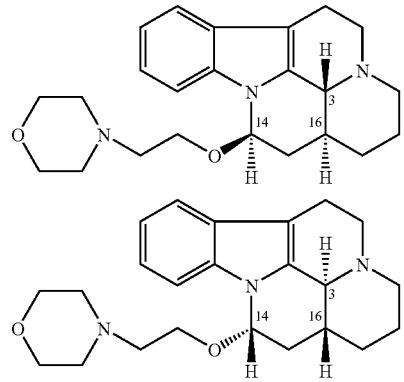

Each enantiomer of the compound (Ie1) is separated by preparative chromatography using a CHIRACEL® OD-H column under the following conditions:

Preparative Liquid Chromatography Method:
Column: 250×20 mm CHIRACEL ® OD-H 5 μm
Mobile phase: Acetonitrile
Flow: 20 ml/min
Detection: UV 300 nm
Temperature: 25° C.

Analytic Liquid Chromatography Method:
Column: 250×4.6 mm CHIRACEL® OD-H 5 μm
Mobile phase: Acetonitrile
Flow: 1.0 ml/min
Detection: TV 230 nm
Temperature: 25° C.

Results:
The following two enantiomers (Ie1a) and (Ie1b) are obtained from 582 mg of the initial product (Table 1).

TABLE 1 characteristics of two enantiomers separated by preparative chiracel HPLC

| First eluted enantiomer (Ie1a) | | Second eluted enantiomer (Ie1b) | |
|---|---|---|---|
| Retention time (min) | 5.87 | Retention time (min) | 6.80 |
| Quantity (mg) | 265 | Quantity (mg) | 264 |
| Chemical purity (% surface area at 230 nm) | 99.3 | Chemical purity (% surface area at 230 nm) | 99.8 |
| Enantiomeric excess (%) | >99.5 | Enantiomeric excess (%) | >99.5 |

EXAMPLE 8

Synthesis of Compound (If1): (±) (3β, 16α) 14,15-dihydro 14-[(2-morpholin-4-yl-ethylcarbamoyl)-methoxy]20,21-dinoreburnamenin

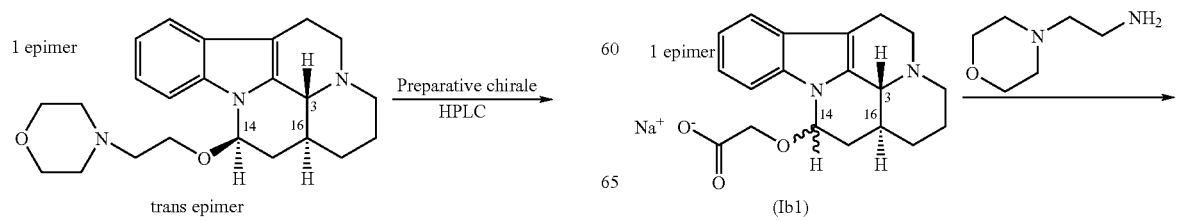

-continued 1 epimer

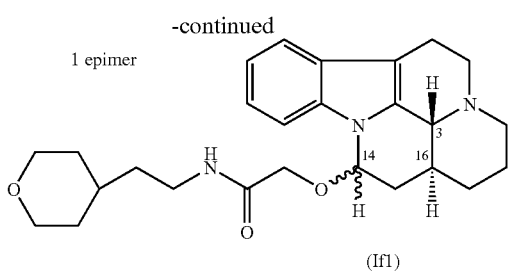

(If1)

The same synthesis is used as for compound (Ic) using 4-(2-aminoethylmorpholin) instead of N-methylpiperazine. The result obtained is 56 mg of yellow powder (If1). Yield: 56%, Melting point: 181° C.-184° C.

RMN $^1$H (400 MHz, CDCl$_3$) δ (ppm) 1.18-1.35 (m, 1H); 1.50-1.71 (m, 1H); 1.75-1.93 (m, 4H); 2.32-2.83 (m, 11H); 2.91-3.17 (m, 3H); 3.38 (m, 2H); 3.55-3.72 (m, 4H); 3.99 (d, 1H, J=14.57 Hz); 4.12 (d, 1H, J=14.57 Hz); 5.69 (m, 1H); 7.13 (m, 3H); 7.35-7.52 (m, 2H).

EXAMPLE 9

Synthesis of Compound (Ii): (±) (3β, 16α) 14,15-dihydro 14-(2-morpholin-4-yl-ethylamino) 20,21-dinoreburnamenin

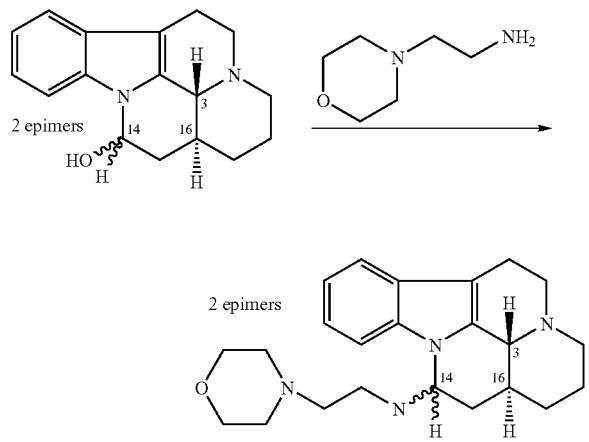

200 mg (0.75 mmol) of compound (1) is dissolved in 4 mL of 4-(2-aminoethyl) morpholine and the reaction mixture is heated to 110° C. for 4 days. The mixture is returned to ambient temperature, and the residue is dissolved with CH$_2$Cl$_2$. The organic phase is washed ten times with water. It is dried on MgSO$_4$, filtered and concentrated. The brown oil obtained is dissolved in ethyl ether, filtered, and the filtrate is concentrated. The brown solid obtained is purified on an eluted silica column with a CH$_2$Cl$_2$/MeOH (98:2) mixture and then a CH$_2$Cl$_2$/MeOH (96:4) mixture. 44 mg of sticky yellow oil is obtained containing the two epimers. Yield: 15%.

RMN $^1$H (300 MHz, CDCl$_3$) δ (ppm) 1.18-1.38 (m, 3H); 1.78-2.81 (m, 17H); 2.93-3.21 (m, 3H); 3.40-3.57 (m, 1H); 3.61-3.78 (m, 3H); 5.18-5.40 (m, 1H); 7.03-7.21 (m, 2H); 7.31-7.64 (m, 2H).

EXAMPLE 10

Pharmacological Protocol

The molecules were selected as a function of their ability to:
1) activate expression of the protein in the Locus Caeruleus (LC) of a Balb/c mouse;
2) their capacity to reveal a significant population of cells in which the phenotype of tyrosine hydroxylase (TH) is restored by the treatment.

The content of TH protein is measured after direct transfer of coronal sections of the frozen brain on nitrocellulose filters. Precise sampling of the protein distribution, revealed by quantitative immunochemistry, was thus done every 80 μm (thus defining each anatomic interval). Quantification was done by using a range of brain homogenates containing an increasing quantity of the TH protein.

The number of immunopositive cells for TH is determined starting from coronal brain sections fixed by immunohistochemistry using the same anatomic sampling.

These analyses are carried out with animals treated by an excipient and with mice treated by a single intraperitoneal injection (20 mg/kg in 100 μl) of the molecule to be tested. The animals are sacrificed three days after the injection.

A typical result is shown on the attached FIG. 1. It clearly shows that the increase in induction of the TH gene takes place in a specific level of the nucleus. The content of TH protein was determined 3 days after a single injection to treated mice and control mice. The quantity of TH protein was determined in each anatomic interval along the caudor-ostral axis. Each bar represents the average value±sem of the control group (black bars) and the treated group (cross-hatched bars). In the Figure, the asterisk <<*>> means that the result is significant (p<0.05); the asterisk <<***>> means that the result is very significant (p<0.0005). An increase of 13±3% of the total TH content in the LC is found (p<0001 using the ANOVA II test).

Biological Activity

All molecules with general formulas (example) were synthesised and sieved ex vivo considering their capacity to induce an increase in the expression of tyrosine hydroxylase (TH) in the Locus Caeruleus (LC) of mice of the inbred Balb/c variety. This genetic model was previously validated as being capable of revealing the capacity of a molecule administered by a peripheral method, to make "dormant" noradrenergic cells appear (Ref. 1 and 2). Table 2 below contains examples of the results of this screening.

TABLE 2

| Molecules | Quantity of TH measured in the LC |
| --- | --- |
| Compound with formula (1) | 120 ± 4 ** |
| Compound with formula (Ia1) | 151 ± 5 ** |
| Compound with formula (Id) | 129 ± 5 ** |
| Compound with formula (Ie1) | 138 ± 4 **** |
| Compound with formula (If1) | 113 ± 4 ** |
| Compound with formula (Ig1) | 118 ± 3 ** |
| Compound with formula (Ij1) | 123 ± 2 ** |

For each of the examples presented in this description, the animals in control groups and the treated animals were injected with 100 μl of the vehicle or a single dose of 20 mg/kg of product by intraperitoneal (i.p.) method. The animals were sacrificed three days after injection, their brain was taken out, frozen and cut into 20 μm frontal sections. In the region containing the LC, sampling was done at 80 μm intervals and the sections were transferred directly onto nitrocellulose filters (Ref. 3). The TH was determined by immunochemistry. The results represent the average±sem obtained on the entire structure in each of the groups treated. They are expressed as a percent of the average value found in the corresponding control group  p<0.02; * p<0.002; **** p<0.0002.

Complementary results were obtained among the examples mentioned using the compound with formula (Ie1) for which acute or sequential administration shows up a significant increase in the population of noradrenergic cells of the locus caeruleus as shown in the Figure below:

The results in FIG. 2 show the posterior-anterior distribution of the number of cells containing TH in the LC determined by immunohistochemistry obtained in a control group of Balb/c mice and in a group of mice treated by the molecule with formula (Ie1). Each bar represents the average obtained in each 80 µm anatomic interval in each experimental group±sem. **** indicates p<0.0001 determined by an ANOVA II (treatment factor). The very significant increase in the number of cells expressing the TH should be noted. In the entire structure, the average values found were equal to 996±1 and 1250±58 in the control group and in the treated group respectively. (Administered dose 20 mg/kg i.p. sequential treatment at D0, D3, D6, D9 and D12, animals sacrificed at D16).

This phenomenon may be stabilised by an appropriate sequential treatment (for example: one 20 mg/kg i.p. injection every 3 days for 15 days, see FIG. 2). Under these conditions, the increase in the number of positive supernumerary TH cells that appeared in the LC is still maintained for 24 days after the treatment stopped.

At the same time as cells reappear in the LC, a very significant increase in the density of noradrenergic fibres can be seen in the prefrontal cortex (FIG. 3) among the animals treated by compound (Ie1).

Figure 3B:
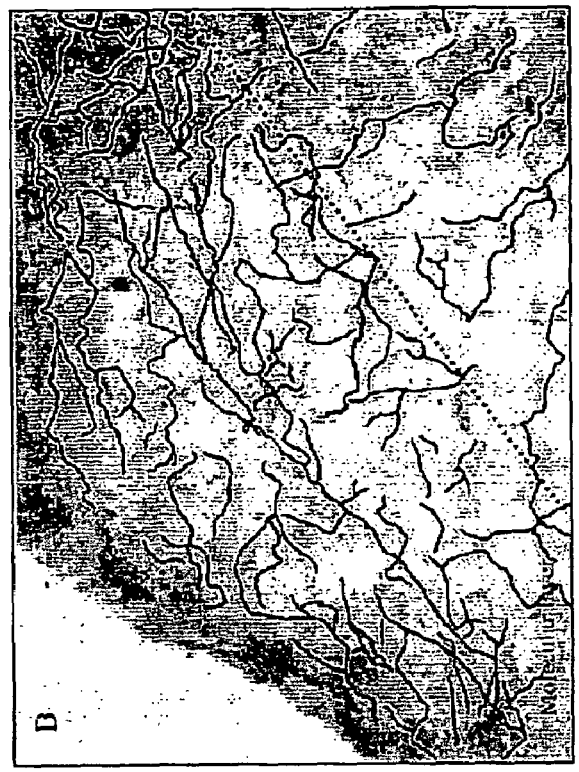
FIGS. 3A and 3B detail the distribution of positive TH fibres on a prefrontal cortex sample of a Balb/c mouse determined by immunohistochemistry, in a control mouse (FIG. 3A) and after sequential treatment by the molecule with formula (Ie1) (FIG. 3B). Positive TH fibres are highlighted. The indication "Molecular Layer" is shown on these figures.
Figure 3A:
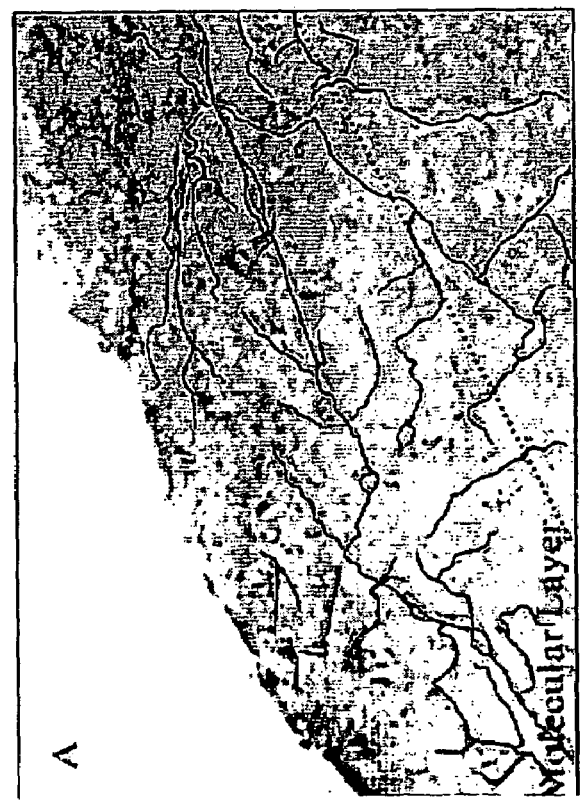

The results in FIG. 3 show the distribution of positive TH fibres on a prefrontal cortex sample of the Balb/c mouse. At left: in a control mouse, the typical orientation (parallel to the surface of the cortex) of noradrenergic fibres identified using an immunocytochemical reaction related to the presence of TH protein, is noticed in the molecular layer of the prefrontal cortex. At right: the Figure shows the increase in the density of positive TH fibres identified in the same cerebral region after a sequential treatment (5 i.p. injections of the molecule (Ie1); 20 mg/kg every three days). The animals were sacrificed three days after the last injection. The dashed lines mark the limit of the molecular layer of the prefrontal cortex.

It was also demonstrated that:
the molecule (Ie1) is active by mouth
this activity is dose dependent by intra-peritoneal (i.p.) method and by oral (p.o.) method. 50% effective (DE50) doses are 0.5 and 1.5 mg/kg respectively. The molecule in the preferred example is thus 30 times more active than its direct synthesis precursor with formula (1) (see Ref. 4, 5 and 6).

Two enantiomer pairs were separated during synthesis of the molecule (Ie). The enantiomer pair with formula (Ie1) was separated into two pure products (Ie1a and Ie1b). The compound (Ie1b) is twice as active as the form (Ie1a) and is thus the preferred form.

The inventors also demonstrated that compounds with formula (I), the radical R of the compound (I) can also represent a hydrogen atom with a double bond between carbon 14 and carbon 15, and particularly the compound (Ie1) has another innovative activity: activation of the expression of hypocretins in a specific population of lateral hypothalamus cells that under normal physiological conditions express these peptides in the balbc/c only slightly, or not at all. This property is shared with its direct synthesis precursor, the compound with formula (1). Table 3 below illustrates this type of result the two chemical entities:

TABLE 3

| Interval | Vehicle | | | | | ANOVA (p) |
| | Number of cells | Sem | Number of cells | Sem | Test t | (4 post. intervals) |
|---|---|---|---|---|---|---|
| | | | Compound (1) | | | |
| 1 | 42.49 | 8.18 | 60.357 | 8.326 | 0.051 | <0.05 |
| 2 | 85.47 | 11.61 | 116.369 | 6.673 | 0.020 | |
| 3 | 149.20 | 11.34 | 177.209 | 11.705 | 0.034 | |
| 4 | 275.75 | 23.01 | 317.237 | 24.075 | 0.118 | |
| 5 | 367.94 | 17.26 | 367.454 | 16.960 | 0.984 | |
| 6 | 398.84 | 18.47 | 377.594 | 14.783 | 0.387 | |
| 7 | 356.35 | 13.23 | 365.523 | 6.777 | 0.549 | |
| 8 | 275.71 | 15.35 | 236.600 | 20.493 | 0.153 | |
| 9 | 124.58 | 11.74 | 136.166 | 11.203 | 0.489 | |
| 10 | 58.43 | 10.42 | 60.840 | 13.779 | 0.891 | |
| 11 | 27.52 | 4.86 | 23.177 | 3.570 | 0.485 | |
| Sum | 2162.23 | 60.21 | 2238.526 | 59.074 | 0.384 | |
| | | | Compound (Ie1) | | | |
| 1 | 15.77 | 2.57 | 31.9 | 7.3 | 0.038 | <0.005 |
| 2 | 60.84 | 5.79 | 63.7 | 13.2 | 0.427 | |
| 3 | 94.08 | 6.01 | 125.1 | 13.0 | 0.033 | |
| 4 | 174.07 | 11.27 | 210.5 | 16.9 | 0.056 | |
| 5 | 309.83 | 7.23 | 331.7 | 9.9 | 0.056 | |
| 6 | 376.87 | 9.98 | 369.9 | 8.3 | 0.299 | |
| 7 | 362.79 | 22.16 | 388.7 | 7.7 | 0.132 | |
| 8 | 343.63 | 24.34 | 322.5 | 14.0 | 0.226 | |
| 9 | 252.37 | 23.00 | 216.3 | 21.1 | 0.136 | |
| 10 | 127.88 | 14.77 | 104.8 | 14.1 | 0.141 | |
| 11 | 64.78 | 10.30 | 56.0 | 11.1 | 0.290 | |
| Sum | 2182.92 | 88.30 | 2221.1 | 57.9 | 0.358 | |

The distribution of cells expressing hypocretins in the lateral hypothalamus is studied here with posterior—anterior sampling in consecutive 80 µm thick intervals. The cells are identified by immunocytochemistry using specific antibodies. The two molecules studied were administered by i.p. method with a single dose of 20 mg/kg. The animals were sacrificed three days after injection. A population of about a hundred supernumerary cells is thus identified at the posterior third of the cerebral core.

The behavioural activity test, the Tail Suspension Test (TST) validated by antidepressants (Ref. 7) in the Balb/c variety, was also done for the molecule in the preferred example (Ie1b) at a dose of 1 mg/kg i.p. The experiment given as an example was carried out three days after a single injection and the effect was compared with the effect of imipramine (30 mg/kg i.p. 30 minutes before the test) (see Table 4 below).

TABLE 4

| | n | Administered dose | Average immobilisation time (s) | Sem | P (student test) |
|---|---|---|---|---|---|
| Vehicle | 8 | 0 | 180 | | |
| Compound (Ie1b) | 7 | 1 mg/kg i.p. | 130 | 15.8 | 0.009 |
| Imipramine | 5 | 30 mg/kg i.p. | 70 | 15.5 | 0.0001 |

The immobilisation time measured during a 6-minute period is significantly reduced three days after a single injection of the compound (Ie1b), the active isomer of racemic (Ie1). The results are the average for n animals.

A receptoral profile done "in vitro" on 74 receptors and channels at a concentration of 10 micromoles of compound (Ie1) indicates that it has no interaction with the voltage dependent Na, K and Ca and SK+Ca channels, nor with catecholamine transport systems, a moderate affinity link may be suspected for the M1 and 5HT5A receptors.

A study of the biodistribution of the molecule (Ie1) 45 minutes after i.p. and os administration at high doses (20 and 60 mg/kg respectively) shows that:
- after i.p. administration of compound (Ie1) in the presence of compound (1), (synthesis precursor) is undetectable.
- after p.o. administration at the same time, the compound (Ie1) represents 89% of the cerebral concentration and compound 1 represents only 11%.
- for compound (Ie1), the cerebral concentration/hepatic concentration ratio is identical in the two administration methods (0.41 and 0.49 respectively).

These results demonstrate that the compounds according to this invention, in which the radical R of compound (I) can also represent a hydrogen atom with a double bond between carbon 14 and carbon 15 and in particular the preferred compound (Ie1) and more particularly (Ie1b), are specifically responsible for the observed effects described above and that their cerebral biodistribution is favourable.

In conclusion, the compounds according to this invention, in which the radical R of the compound (I) may also represent a hydrogen atom with a double bond between carbon 14 and carbon 15, and in particular the preferred compound (Ie1) and more particularly (Ie1b), are capable of inducing a plasticity phenomenon into the brain that enables resurgence of a quiescent population of noradrenergic cells of the cerulean complex in the brain of Balb/c mice. This phenotypical awakening is associated with an increase in the noradrenergic innervation of the prefrontal cortex in this genetically pure mutant line of mice that has a low density of this front innervation. A preferred compound was identified. It is activated by os. It is thirty times more active than its direct chemical precursor that has similar properties. These compounds according to this invention, in which the radical R of compound (I) can also represent a hydrogen atom with a double bond between carbon 14 and carbon 15, are also capable of long-term activation of a specific population of neurons expressing hypocretins in the lateral hypothalamus.

Considering the potential efficiency of this family on central noradrenergic mediation, particularly prefrontal, and on hypocretinergic neurons for which implications in the sleep—wake cycle and animal depression models are known (Ref. 8, 9). Considering the particular controls applied in man by noradrenergic neurons in control of the humour (Ref. 10, 11) and cognitive phenomena (Ref. 12). Considering the direct evidence of functional frontal and pre-frontal deficits in several psychiatric and neurological pathologies, previously observed deficits in the locus caeruleus in severe depression (Ref. 10, 11, 12) and in major degenerative syndromes such as Alzheimer's disease and Parkinson's disease (Ref. 12, 13). Since there is a large number of patients resistant to currently available therapies, the compounds according to this invention in which the radical R of compound (I) can represent also a hydrogen atom with a double bond between carbon 14 and carbon 15 and in particular, the preferred compound (Ie1) and more particularly (Ie1b) are useful for the prevention or treatment of depressive syndromes and particularly major depressions, resistant depressions like those defined in DSM4 (Ref. 14, 15, 16) and for normalisation of the negative symptoms of bipolar depressions (Ref 17) and schizophrenia (Ref. 18). This type of molecule is also useful for the treatment of symptomatic frontal disorders in their cognitive components (Mild Cognitive Impairment (Ref. 9); pre-dementia and dementia conditions related to Alzheimer's disease or Parkinson's disease (Ref. 20)) or behaviour disorders including hypoactivity, attention problems, characterical problems (of the Attention deficit-Hyperactivity (ADHD) type (Ref. 21)), and in sleep problems particularly in hypoactivity or characterised hypersomnia (narcolepsy).

BIBLIOGRAPHY

1. Ginovart N, Marcel D, Bezin L, Garcia C, Gagne C, Pujol J F, Weissmann D. Tyrosine hydroxylase expression within Balb/c and C57black/6 mouse locus coeruleus. I. Topological organisation and phenotypic plasticity of the enzyme-containing cell population. Brain Res. 1996 May 20; 721 (1-2): 11-21.
2. Ginovart N, Marcel D, Bezin L, Gagne C, Pujol J F, Weissmann D. Tyrosine hydroxylase expression within Balb/c and C57black/6 mouse locus coeruleus. II. Quantitative study of the enzyme level. Brain Res. 1996 May 6; 719(1-2): 45-55.
3. Weissmann D, Labatut R, Richard F, Rousset C, Pujol J F. Direct transfer into nitrocellulose and quantitative radioautographic anatomical determination of brain tyrosine hydroxylase protein concentration. J. Neurochem. 1989 September; 53 (3): 793-9.
4. Bourde O., Schmitt P and Pujol J F. Long-term effect of RU24722 on tyrosine hydroxylase protein concentration in the locus coeruleus of mice: Differential results in Balb/c, C57BL/6 and their CB6 F1 hybrid. Neurochem Int. 1991, 19, (1), 25-31.
5. Labatut R, Richard F, Milne B, Quntin L, Lecestre D, Pujol J F. Long-term effects of RU24722 on tyrosine hydroxylase of the rat brain. J. Neurochem. 1988 November; 51(5): 1367-74.
6. Schmitt P, Reny-Palasse V, Bourde O, Garcia C, Pujol J F. Further characterisation of the long-term effect of RU24722 on tyrosine hydroxylase in the rat locus coeruleus. J. Neurochem. 1993 October; 61(4): 1423-9.
7. X. Liu and H. K. Gershenfeld: Genetic Differences in the Tail-Suspension Test and Its Relationship to Imipramine Response among 11 Inbred Strains of Mice: Biol. Psychiatry 2001 49, 575-581.
8. J. S. Allard Y Tizabio, J P Shaffery, C. O. Trouth, K. Manabe. Stereological analysis of hypothalamic hypocretin/orexin neurons in animal models of depression Neuropeptides 2004, 38, 311-315.
9. D. Chabas, S. Taheri, C. Renier, and E. Mignot. The genetic narcolepsie: An Rev. Genomics Human Genet. 2003, 4, 459-83.
10. Arango V, Underwood M D, Mann J, Fewer pigmented locus coeruleus neurons in suicide victims: preliminary results. Biol Psychiatry 1996, 39 112-120.
11. Mann J. J. Neurobiology of suicidal behavior, Nature Reviews/Neuroscience 4, 2003, 820-28.
12. Marc R. Mariena*, Francis C. Colpaerta, Alan C. Rosenquist Noradrenergic mechanisms in neurodegenerative diseases: a theory: Brain Research Reviews 45 (2004) 38-78.
13. M. Gesi, P. Soldani, F-S Giorgi, A. Santinami, I. Bonaccorsi and F. Fornai. The role of the locus coeruleus in the development of Parkinson's disease. Neuroscience & Biobehavioral Reviews, Volume 24, Issue 6, August 2000, Pages 655-668.

14. The fourth edition of the Diagnostic and Statistical Manual of mental Disorder-American Psychiatric Association Publisher. Washington D.C.

15. Fava M, Davidson K G. Definition and epidemiology of treatment-resistant depression Psychiatry Clin North Am. 1996, June; 19(2): 179-20.

16. Fava M, Davidson K G. Definition and epidemiology of treatment-resistant depression Psychiatry Clin North Am. 1996, June; 19(2): 179-200.

17. Kettera T A and Drevets W C, Clinical Neuroscience Research 2 (2002) 182-192 Neuroimaging studies of bipolar depression: functional neuropathology, treatment effects, and predictors of clinical response Clinical Neuroscience Research 2 (2002) 182-192.

18. J. D. Cohen R. Ganguli C. Carter J. Brar T Nichols M. DeLeo M. Mintun: Hypofrontality and working memory dysfunction in schizophrenia Biological Psychiatry, Volume 37, Issue 9, 1 May 1995, Page 633.

19. Ronald C. Petersen: Mild cognitive impairment: clinical trials: Nature reviews |Drug Discovery volume 2| August 2003 647.

20. Vjera A. Holthoff, Bettina Beuthien-Baumann, Elke Kalbe, Susanne Lüdecke, Olaf Lenz, Gerhard Zündorf, Sebastian Spirling, Kristin Schierz, Peter Winiecki, Sandro Sorbi, and Karl Herholz: Regional Cerebral Metabolismin Early Alzheimer's Disease with Clinically Significant Apathy or Depression: BIOL PSYSCHIATRY 2005;57: 412-421.

21. Eve M. Valera, Stephen V. Faraone, Joseph Biederman, Russel A. Poldrack, and Larry J. Seidman: Functional Neuroanatomy of Working Memory in Adults with Attention-Deficit/Hyperactivity Disorder: Biol Psychiatry 2005; 57: 439-447.

What is claimed is:

1. A compound of formula (I)

(I)

its isomers, enantiomers, diastereoisomers and mixtures thereof;

wherein R represents an —AR' radical, A represents an oxygen, sulphur, or nitrogen atom and R' is selected from the group consisting of a) linear or branched $C_1$-$C_6$ alkyl radicals, $C_2$-$C_6$ alkenyl radicals and $C_2$-$C_6$ alkynyl radicals and linear or branched arylalkyl, alkoxyarylalkyl, heteroarylakyl and heterocycloalkyl radicals, b) esters of the formula —$R_1$—CO—O—$R_2$, wherein $R_1$ represents a radical selected from the group consisting of linear or branched $C_1$-$C_6$ alkylene radicals, $C_2$-$C_6$ alkenylene radicals and $C_2$-$C_6$ alkynylene radicals and $R_2$ represents a radical selected from the group consisting of hydrogen, linear or branched $C_1$-$C_6$ alkyl radicals, $C_2$-$C_6$ alkenyl radicals, $C_2$-$C_6$ alkynyl radicals and $C_3$-$C_{12}$ cycloalkyl radicals, c) amides of the formula $$—R_3—CO—N\begin{matrix}Z\\ Y\end{matrix}$$

wherein $R_3$ is selected from the group consisting of linear or branched $C_1$-$C_6$ alkyl radicals, $C_2$-$C_6$ alkenylene radicals and $C_2$-$C_6$ alkynylene radicals wherein Y represents a radical selected from the group consisting of hydrogen, linear or branched $C_1$-$C_6$ alkyl radicals, $C_2$-$C_6$ alkenyl radicals and $C_2$-$C_6$ alkynyl radicals and linear or branched aryl, arylalkyl, heteroarylalkyl and heterocycloalkyl radicals, wherein Z is selected from the group consisting of hydrogen, linear or branched $C_1$-$C_6$ alkyl radicals, $C_2$-$C_6$ alkenyl radicals and $C_2$-$C_6$ alkynyl radicals and linear or branched aryl, arylalkyl, heteroarylalkyl and heterocycloalkyl radicals, provided that Y and Z together may form a $C_3$-$C_6$ cycloalkyl radical or a $C_3$-$C_6$ heterocyclic radical which can be optionally substituted by one or more $C_1$-$C_6$ alkyl, aryl, heteroaryl or halogen radicals and d) a radical selected from the group consisting of linear or branched $C_{1-C6}$ alkyl radicals, $C_2$-$C_6$ alkenyl radicals and $C_2$-$C_6$ alkynyl radicals, substituted by at least one amine of the formula $$—N\begin{matrix}Z\\ Y\end{matrix}$$

wherein Y and Z are as described above; and
pharmaceutically acceptable salts.

2. The compound according to claim 1, wherein R' represents a group with formula $R_1$—CO—O—$R_2$, in which $R_1$ represents $C_1$-$C_6$ alkylene radical.

3. The compound of claim 2, wherein the $C_1$-$C_6$ radical is —$CH_2$—.

4. The compound according to claim 1, wherein $R_2$ is a hydrogen atom or a $C_1$-$C_6$ alkyl radical.

5. The compound according to claim 1, wherein R' represents an amide of the formula $$—R_3—CO—N\begin{matrix}Z\\ Y\end{matrix}$$

wherein Y and Z together form a $C_3$-$C_6$ heterocyclic radical.

6. The compound according to claim 5, wherein the heterocylic radical is substituted by one or more $C_1$-$C_6$ alkyl radicals.

7. The compound according to claim 1, wherein —R' represents an amino-alkyl radical selected from the group consisting of $C_1$-$C_6$ alkyl radicals substituted by at least one amine of the formula

wherein Y and Z together form a $C_2$-$C_6$ heterocyclic radical.

8. The compound according to claim 7, wherein the heterocyclic radical is substituted by one or more $C_1$-$C_6$ alkyl radicals.

9. The compound according to claim 1, wherein —R' represents a heteroarylalkyl radical.

10. The compound according to claim 1, wherein the compound is selected from the group consisting of:

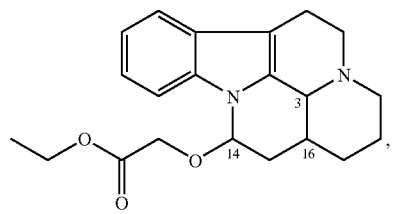

(Ia)

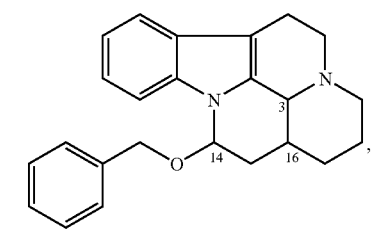

(Id)

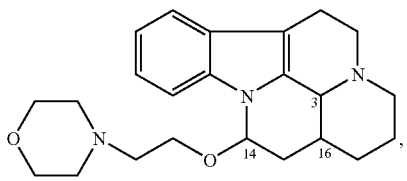

(Ie)

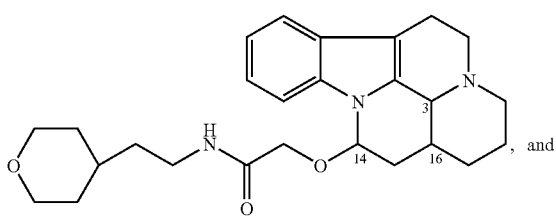

(If)

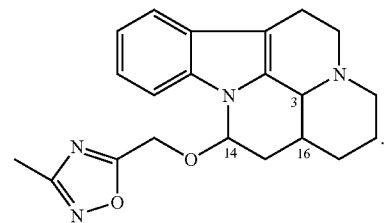

(Ig)

11. The compound according to claim 1, wherein the hydrogen atom in position 3 and the hydrogen atom in position 16 are in the trans position and the radical R in position 14 is in the α or β form.

12. The compound according to claim 1, wherein the compound with formula (I) or one of its pharmaceutically acceptable salts is in the form of a racemic mixture or optically active isomer.

13. The compound according to claim 1, wherein the compound with formula (I) or one of its pharmaceutically acceptable salts is one of:
   a) a compound having the dextrorotatory and/or levorotatory form (3α); and
   b) a compound in the dextrorotatory and/or levorotatory form (16α), and in which the mixture of the two levorotatory and dextrorotatory diastereoisomers present in compounds a) and b) is or is not in equimolar proportion.

14. The compound according to claim 1, wherein the compound with formula (I) or one of its pharmaceutically acceptable salts is one of:
   a) a compound in the form (3α, 14α);
   b) a compound in the form (3α, 14β);
   c) a compound in the form (14α, 16α); and
   d) a compound in the form (14β, 16α).

15. The compound according to claim 10, wherein the compound of formula (I) or one of its pharmaceutically acceptable salts represents the epimer (Ie1) comprising the enantiomer pair (3α, 14β) and (16α, 14α) selected from the formulas

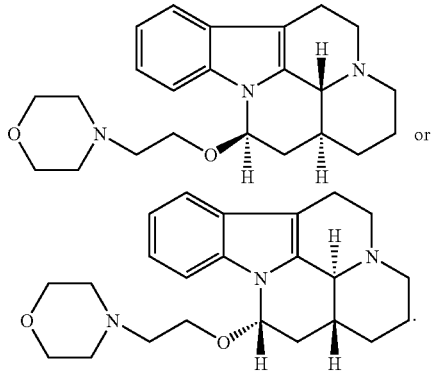

16. The compound according to claim 15, wherein the compound of formula (I) or one of its pharmaceutically acceptable salts represents the enantiomer (Ie1b) that is the second eluted compound when the enantiomer mixture (Ie1) is subjected to a HPLC chromatography utilizing a column in which the stationary phase is composed of silica gel particles on which tris(2,5-dimethylphenylcarbamate) cellulose is grafted, the mobile phase used being acetonitrile.

17. A pharmaceutical composition comprising a compound according to claim 1 and a pharmaceutically acceptable excipient.

18. A method for the treatment of depression comprising the step of administering a therapeutically effective amount of a compound according to claim 1 to a patient to treat depression.

19. A method according to claim 18, wherein the compound is administered by oral, intravenous, intraperitoneal or intramuscular application.

20. A method according to claim 18, wherein the compound is administered to a patient in dosages of about 20 to about 60 mg.

* * * * *